US011087882B1

(12) United States Patent
Perlin et al.

(10) Patent No.: US 11,087,882 B1
(45) Date of Patent: Aug. 10, 2021

(54) SIGNAL PROCESSING FOR MAKING PREDICTIVE DETERMINATIONS

(71) Applicant: C/HCA, Inc., Nashville, TN (US)

(72) Inventors: Jonathan Perlin, Nashville, TN (US); Deborah Reiner, Nolensville, TN (US); Jim Najib Jirjis, Nashville, TN (US); Edmund Stephen Jackson, Nashville, TN (US); William Michael Gregg, Nashville, TN (US); Thomas Andrew Doyle, Franklin, TN (US); Paul Martin Paslick, Nashville, TN (US); Brian Freeman, Nashville, TN (US); Victoria Samples, Nashville, TN (US)

(73) Assignee: C/HCA, Inc., Nashville, TN (US)

( * ) Notice: Subject to any disclaimer, the term of this patent is extended or adjusted under 35 U.S.C. 154(b) by 0 days.

(21) Appl. No.: 16/913,989

(22) Filed: Jun. 26, 2020

Related U.S. Application Data

(63) Continuation-in-part of application No. 16/450,314, filed on Jun. 24, 2019, now abandoned, which is a continuation-in-part of application No. 15/829,733, filed on Dec. 1, 2017, now abandoned, and a continuation-in-part of application No. 15/674,326, filed on Aug. 10, 2017, now Pat. No. 10,783,998, which is a continuation-in-part of application No. 15/299,324, filed on Oct. 20, 2016.

(60) Provisional application No. 62/428,911, filed on Dec. 1, 2016, provisional application No. 62/244,645, filed on Oct. 21, 2015.

(51) Int. Cl.
*H04L 29/06* (2006.01)
*G16H 50/20* (2018.01)
*G16H 15/00* (2018.01)
*H04L 29/08* (2006.01)

(52) U.S. Cl.
CPC ............. *G16H 50/20* (2018.01); *G16H 15/00* (2018.01); *H04L 67/12* (2013.01)

(58) Field of Classification Search
CPC ......... G16H 50/20; G16H 15/00; H04L 67/12
See application file for complete search history.

(56) References Cited

U.S. PATENT DOCUMENTS

| | | | |
|---|---|---|---|
| 8,229,760 B2 | 7/2012 | Hasan et al. | |
| 8,311,855 B2 | 11/2012 | Kerr et al. | |
| 8,504,386 B2 | 8/2013 | Manning et al. | |
| 8,527,292 B1 | 9/2013 | Ozden | |
| 8,788,287 B2 | 7/2014 | Padate et al. | |
| 8,924,236 B2 | 12/2014 | Marchosky | |
| 8,959,027 B2 | 2/2015 | Kusens | |
| 9,355,007 B1 * | 5/2016 | Eicher ................. | G06F 11/3428 |

(Continued)

OTHER PUBLICATIONS

Non-Final Office Action dated Jan. 5, 2018 in U.S. Appl. No. 15/674,326, all pgs.

(Continued)

*Primary Examiner* — Kim T Nguyen
(74) *Attorney, Agent, or Firm* — Kilpatrick Townsend & Stockton, LLP

(57) ABSTRACT

In some examples, unstructured data is evaluated using a natural language processing model to output a set of subjective indicators. These subjective indicators are scored using a predictive model to determine whether a dependent user has or is likely to develop a particular condition such as a cellular abnormality.

20 Claims, 13 Drawing Sheets

(56) References Cited

U.S. PATENT DOCUMENTS

| | | | |
|---|---|---|---|
| 9,406,097 | B1 | 8/2016 | Piety |
| 10,097,497 | B1 | 10/2018 | Son |
| 2005/0288965 | A1 | 12/2005 | Eaton et al. |
| 2006/0036619 | A1 | 2/2006 | Fuerst |
| 2006/0080267 | A1 | 4/2006 | Nelken |
| 2006/0161457 | A1 | 7/2006 | Rapaport |
| 2006/0266826 | A1 | 11/2006 | Banfield |
| 2007/0150311 | A1 | 6/2007 | Lazerus |
| 2008/0104052 | A1 | 5/2008 | Ryan |
| 2011/0046979 | A1 | 2/2011 | Tulipano et al. |
| 2011/0125528 | A1 | 5/2011 | Padate et al. |
| 2011/0246230 | A1 | 10/2011 | Sie et al. |
| 2013/0096943 | A1 | 4/2013 | Carey |
| 2014/0081667 | A1 | 3/2014 | Joao |
| 2014/0279920 | A1* | 9/2014 | Madhavarapu ..... G06F 11/1458 707/649 |
| 2015/0100329 | A1 | 4/2015 | Dreyfuss et al. |
| 2015/0169827 | A1 | 6/2015 | LaBorde |
| 2015/0213225 | A1 | 7/2015 | Amarasingham et al. |
| 2015/0310176 | A1 | 10/2015 | Chen et al. |
| 2015/0339586 | A1 | 11/2015 | Adjaoute |
| 2016/0321430 | A1 | 11/2016 | Eckman et al. |
| 2016/0342753 | A1 | 11/2016 | Feazell |
| 2016/0364544 | A1 | 12/2016 | Das et al. |
| 2017/0116373 | A1 | 4/2017 | Ginsburg et al. |
| 2017/0124269 | A1 | 5/2017 | McNair et al. |

OTHER PUBLICATIONS

Final Office Action dated Jun. 25, 2018 in U.S. Appl. No 15/674,326, all pgs.

Non-Final Office Action dated Jun. 1, 2020 in U.S. Appl. No 15/299,324, all pgs.

McCoy, et al, "Sentiment Measured in Hospital Discharge Notes is Associated with Readmission and Mortality Risk: An Electronic Health Record Study" PLOS ONE, DOI:10.1371/journal.pone.0136341, Aug. 24, 2015, 10 pages.

Tsui, et. al., "Technical Description of RODS: A Real-Time Public Health Surveillance System", (Year 2003), all pgs.

"A Context-Aware Middleware-level Solution Towards a Ubiquitous Healthcare System" (Year:2009), all pgs.

Marafino, et. al., Efficient and Sparse Features Selection for Biomedical Text Classification via the Elastic Net: Application to ICU Risk Stratification from Nursing Notes (Year: 2015), all pgs.

Carrel, et al, "Using Natural Language Processing to Improve Efficiency of Manual Chart Abstraction in Research: the Case of Breast Cancer Recurrence", 2014, all pgs.

Coden, et al, "Automatically Extracting Cancer Disease Characteristics into a Disease Knowledge Representation Model", 2008, all pgs.

Hoogendoorn, et al, "Utilizing Uncoded Consultation Notes From Electronic Medical Records for Predictive Modeling of Colorectal Cancer", 2016, all pgs.

Jha, et al, "Cancer Stage Prediction Based on Patient Online Discourse", 2010, all pgs.

Morante, et al, "Learning the Scope of Hedge Cues in Biomedical Texts", 2010, all pgs.

Ong, et al, "The Colorectal Cancer Recurrence Support (CARES) System", 1997, all pgs.

Zhao et al, "Combining PubMed knowledge and EHR Data to Develop a Weighted Bayesian Network for Pancreatic Cancer Prediction", 2011, all pgs.

Zheng et al, "Effective Information Extraction Framework for Heterogeneous Clinical Reports Using Online Machine Learning and Controlled Vocabularies", 2017, all pgs.

Office of the National Coordinator for Health Information Technology, "Improving Hospital Transitions and Care Coordinations Using Automated Admission, Discharge, and Transfer Alerts (Year: 2013)".

Advisory Action dated Oct. 1, 2018 in U.S. Appl. No. 15/674,326, all pgs.

Non-Final Office Action dated Jan. 9, 2019 in U.S. Appl. No. 15/674,326, all pgs.

Final Office Action dated Jun. 28, 2019 in U.S. Appl. No. 15/674,326, all pgs.

Non-Final Office Action dated Apr. 15, 2020 in U.S. Appl. No. 15/829,733, all pgs.

First Action Interview Pilot Program Pre-Interview Communication dated Aug. 28, 2019 in U.S. Appl. No. 16/450,314, all pgs.

Final Office Action dated Feb. 26, 2020 in U.S. Appl. No. 16/450,314, all pgs.

Non-Final Office Action dated Jan. 2, 2020 in U.S. Appl. No. 15/674,326, all pgs.

Notice of Allowance dated May 5, 2020 in U.S. Appl. No. 15/674,326, all pgs.

* cited by examiner

SIGNAL PROCESSING FOR MAKING PREDICTIVE DETERMINATIONS

CROSS-REFERENCES TO RELATED APPLICATIONS

The present application is a continuation-in-part application which claims the priority benefit under 35 U.S.C. 119(e) to U.S. Ser. No. 15/674,326, filed Aug. 10, 2017, which is a continuation-in-part application which claims the priority benefit under 35 U.S.C. 119(e) to U.S. Ser. No. 15/299,324, filed on Oct. 20, 2016, which claims priority to U.S. Provisional Application No. 62/244,645, filed on Oct. 21, 2015. The present application is also a continuation-in-part application which claims the priority benefit under 35 U.S.C. 119(e) to U.S. Ser. No. 16/450,314, filed Jun. 24, 2019, which is a continuation-in-part of U.S. Ser. No. 15/829,733, filed Dec. 1, 2017, which claims priority to U.S. Provisional Application No. 62/428,911, filed on Dec. 1, 2016. The entire disclosures of each of the above applications are incorporated by reference herein in their entirety for all purposes.

BACKGROUND

This specification relates in general to making predictive determinations and, but not by way of limitation, to making predictive determinations pertaining to dependent users.

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored or streamed data can create inefficiencies and the fact that other data may typically be ignored or abandoned may create undesirable outcomes.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. In a first example, a system, includes: a memory configured to store computer-executable instructions; and a processor configured to access the memory to execute the computer-executable instructions to perform operations. The operations include accessing a data stream including messages originating from a plurality of sending systems in a computer network. The operations also include identifying a particular message from among the messages in the data stream based on a message type associated with the particular message, the particular message including a note that includes an observation corresponding to a dependent user as observed and recorded by an authorized user, at least a portion of the observation represented as unstructured data in the note. The operations also include evaluating the unstructured data in the note using a natural language processing model to identify subjective indicators present in the note, the subjective indicators indicating an assessment, a plan, or sentiment of the authorized user with respect to the dependent user and a cellular abnormality, the cellular abnormality being a cellular condition potentially present in the dependent user. The operations also include assigning a weight value to each of the identified subjective indicators based on a respective correspondence of the identified subjective indicators to the cellular abnormality. The operations also include determining a composite abnormality score based on weight values of the identified subjective indicators and relationships between the identified subjective indicators, the composite abnormality score corresponding to a presence of the cellular abnormality in the dependent user. The operations also include determining whether the cellular abnormality is present in the dependent user based on a first comparison of the composite abnormality score with a normality threshold. The operations also include generating a cellular abnormality report that identifies at least the presence of the cellular abnormality and the dependent user.

In a second example, a computer-implemented method is provided. The computer-implemented method includes accessing a data stream including messages originating from a plurality of sending systems in a computer network. The computer-implemented method also includes identifying a particular message from among the messages in the data stream based on a message type associated with the particular message, the particular message including a note that includes an observation corresponding to a dependent user as observed and recorded by an authorized user, at least a portion of the observation represented as unstructured data in the note. The computer-implemented method also includes evaluating the unstructured data in the note using a natural language processing model to identify subjective indicators present in the note, the subjective indicators indicating an assessment, a plan, or sentiment of the authorized user with respect to the dependent user and a cellular abnormality, the cellular abnormality being a cellular condition potentially present in the dependent user. The computer-implemented method also includes assigning a weight value to each of the identified subjective indicators based on a respective correspondence of the identified subjective indicators to the cellular abnormality. The computer-implemented method also includes determining a composite abnormality score based on weight values of the identified subjective indicators and relationships between the identified subjective indicators, the composite abnormality score corresponding to a presence of the cellular abnormality in the dependent user. The computer-implemented method also includes determining whether the cellular abnormality is present in the dependent user based on a first comparison of the composite abnormality score with a normality threshold. The computer-implemented method also includes generating a cellular abnormality report that identifies at least the presence of the cellular abnormality and the dependent user.

In a third example, one or more non-transitory computer-readable storage media including computer executable instructions is provided. The computer-executable instructions when executed by one or more computer systems cause the one or more computer systems to perform operations including accessing a data stream including messages originating from a plurality of sending systems in a computer network. The operations also include identifying a particular message from among the messages in the data stream based on a message type associated with the particular message, the particular message including a note that includes an observation corresponding to a dependent user as observed and recorded by an authorized user, at least a portion of the observation represented as unstructured data in the note. The operations also include evaluating the unstructured data in the note using a natural language processing model to identify subjective indicators present in the note, the subjective indicators indicating an assessment, a plan, or sentiment of the authorized user with respect to the dependent user and a cellular abnormality, the cellular abnormality being a cellular condition potentially present in the dependent user. The operations also include assigning a weight value to each of the identified subjective indicators based on a respective correspondence of the identified subjective indicators to the cellular abnormality. The operations also include determining a composite abnormality score based on weight values of the identified subjective indicators and relationships between the identified subjective indicators, the composite abnormality score corresponding to a presence of the cellular abnormality in the dependent user. The operations also include determining whether the cellular abnormality is present in the dependent user based on a first comparison of the composite abnormality score with a normality threshold. The operations also include generating a cellular abnormality report that identifies at least the presence of the cellular abnormality and the dependent user.

BRIEF DESCRIPTION OF THE DRAWINGS

Various examples in accordance with the present disclosure will be described with reference to the drawings, in which.

DETAILED DESCRIPTION

The ensuing description provides preferred exemplary example(s) only, and is not intended to limit the scope, applicability or configuration of the disclosure. Rather, the ensuing description of the preferred exemplary example(s) will provide those skilled in the art with an enabling description for implementing a preferred exemplary example. It is understood that various changes may be made in the function and arrangement of elements without departing from the spirit and scope as set forth in the appended claims.

Figure 1:
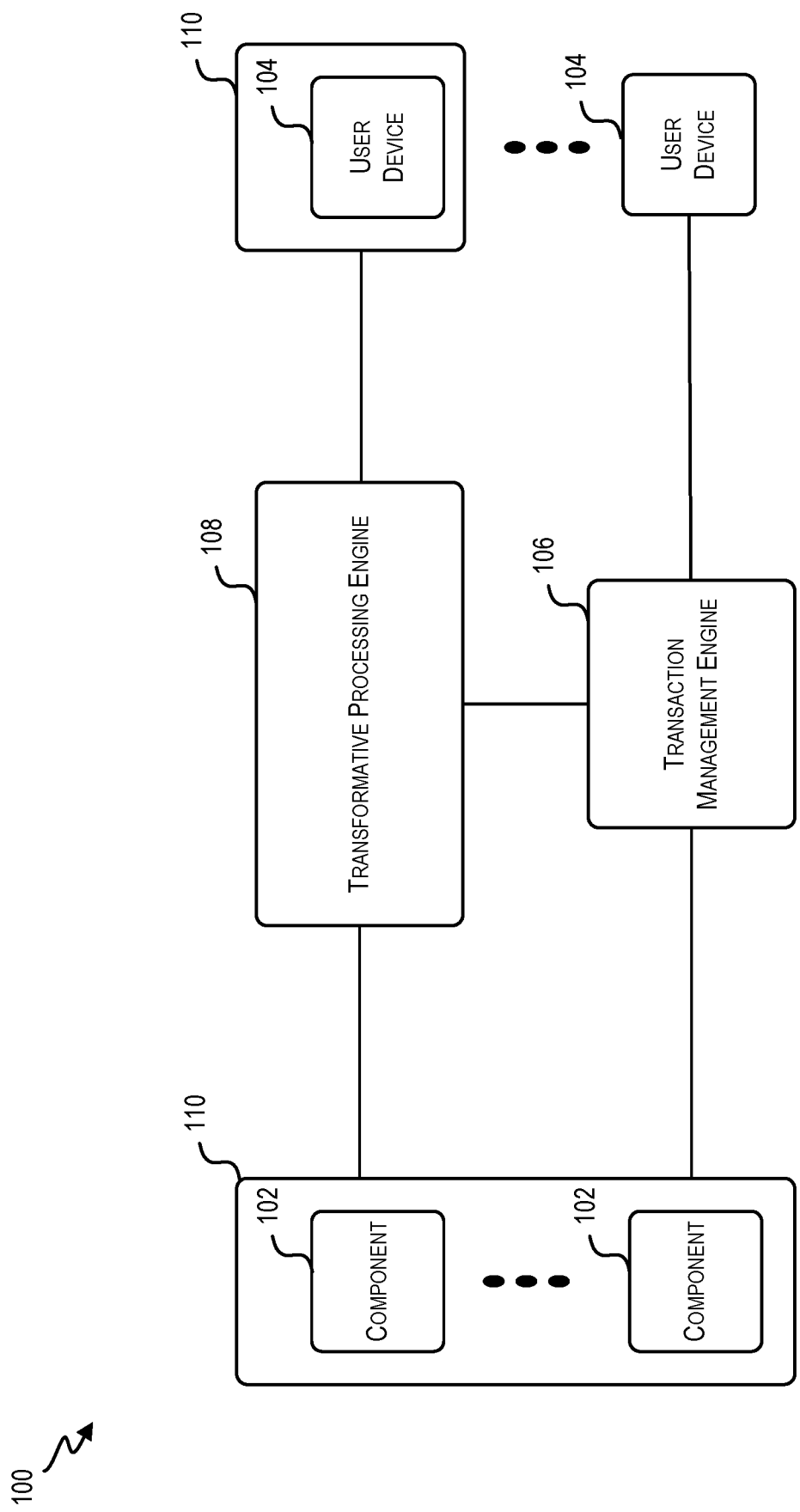
FIG. 1 is an example block diagram illustrating an interaction system in which techniques relating to signal processing for making predictive determinations may be implemented, according to at least one example.

Referring first to FIG. 1, a block diagram of an example of an interaction system 100 is illustrated. Generally, in interaction system 100, data can be generated at one or more system components 102 and/or user devices 104. Transaction management engine 106 can manage the flow of communications within interaction system. Transformative processing engine 108 can receive, intercept, track, integrate, process and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102 and/or data in a corresponding communication received from a user device.

As another example, a user device 104 can be configured to detect user input received at a user interface of the device. The user input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect user input requesting particular data, to generate a request communication (e.g., to be sent to transformative processing engine), to receive the requested data and/or to present the received data.

Data can include information that identifies a person, such as personal information and/or demographic information. For example, the information can identify a person's name, age, sex, race, physical address, phone number, email address and/or social security number. Data may include information collected by a government agent, employer, insurer, or school or university, that relates to a past, present, or future condition or status (e.g., pertaining to employment, political involvement, occupation, health, or financial status) of any individual. For example, data may include information about past events.

Data may identify an entity being evaluated and/or one at least partly performing an evaluation. For example, a communication may identify a first company as one being evaluated and a second company as one evaluating a quality of a product of the first company. As another example, a communication may identify a first service plan of a first company as one providing an Internet network and may identify one or more users providing speed checks over the network.

The depicted engines, devices and/or components can communicate over one or more networks. A network of one or more networks can include a wired network (e.g., fiber, ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or transaction management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or processing focus. Exemplary types of facilities include server farm facilities, web-server facilities, data-storage facilities, technical-support facilities, telecommunication facilities, care facilities and/or business operation facilities. For example, a first facility may include a structure at a first location at which one or more resources (e.g., computational resources, equipment resources, laboratory resources and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another examples, different facilities may include resources of similar or same types but may vary in terms of, for example, user accessibility, location, managing client, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client or receiving a service from the client.

In some examples, one or more components 102 and one or more user devices 104 may communicate with transformative processing engine 108 and transaction management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., transaction management engine 106, an entity device and/or a user device) and/or locally or remotely stored. In some examples, transformative processing engine 108 receives data in a particular format (e.g., the Health Level 7 (HL7) format or other format) or conforming to any other suitable format and/or is configured to transform received data to conform with the particular format.

One or more components 102 of facility 110 can include and/or has access to a local or remote memory for storing generated data. In some examples, the data is stored by one or more servers local to facility 110. Such storage may enable facility 110 to retain locally data pertaining to its facility prior to (or in conjunction with) the data being shared with transformative processing engine 108 and/or transaction management engine 106. In some examples, the one or more servers of facility 110 share data directly with a record service (not shown), and the record service makes the data available to transformative processing engine 108 and/or transaction management engine 106. Once an electronic record is updated at facility 110, an indication of the update may be provide to the record service. The record service may then update a corresponding record associated with the electronic record.

The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from an component (or facility), the record service can identify a corresponding record and update the record to include the data (or processed version thereof). In some examples, the record service provides data to transformative processing engine 108.

Facility 110 can include one at which a resource is located and/or service is provided. Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private and/or proprietary network or protocols. The use of one or more private and/or proprietary protocols can promote secure transfer of data.

Figure 2:
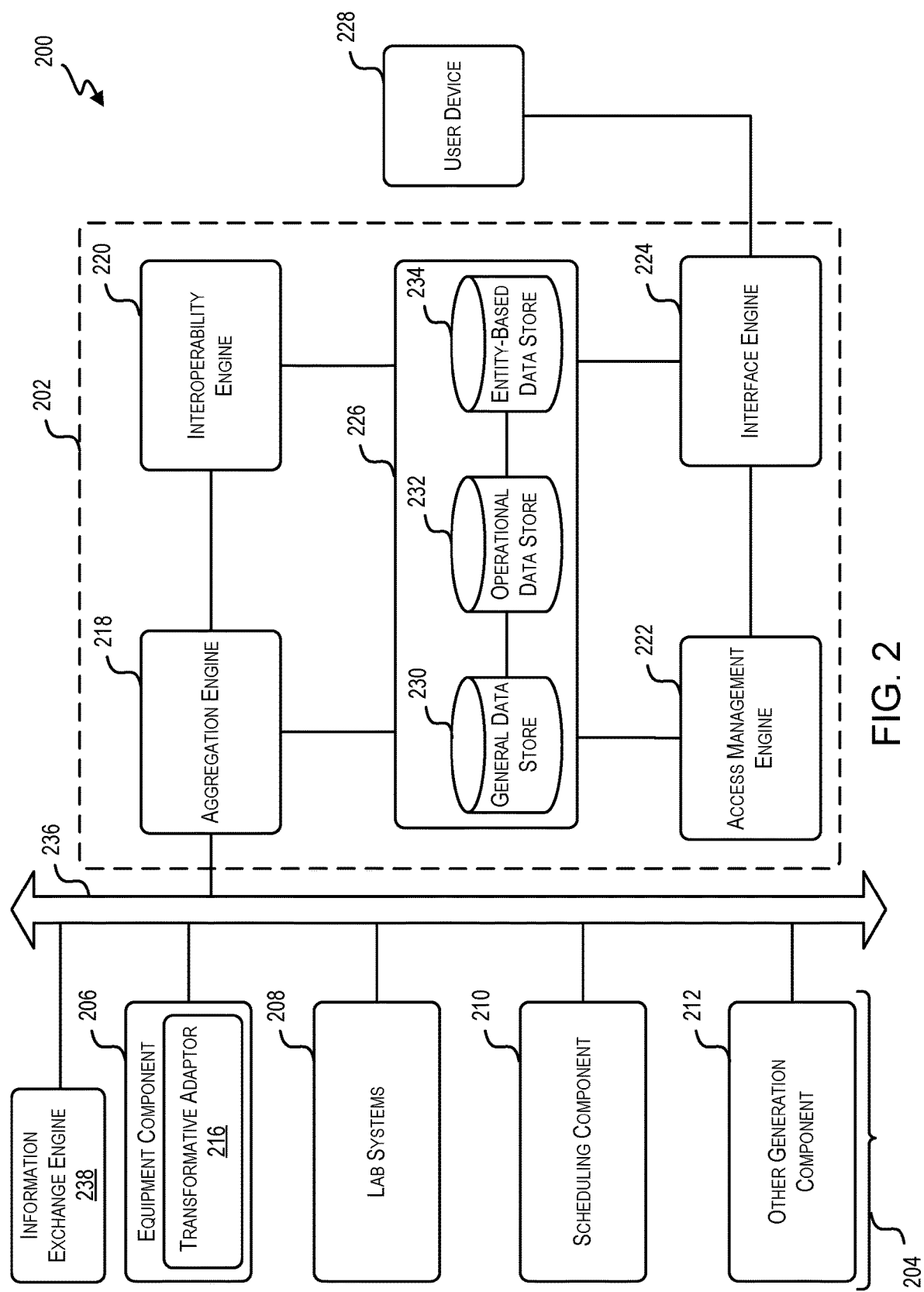
FIG. 2 is an example block diagram illustrating an interaction system in which techniques relating to signal processing for making predictive determinations may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 includes an equipment component 206, a lab systems component 208, a scheduling component 210 and other generation component 212. One or more generation components 204 are examples of one or more components 102 discussed with reference to FIG. 1.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus. The messaging bus, which may be included in the transformative processing engine 202 or separate, is able to see data that moves throughout the interaction system 200. The messaging bus also includes a subscription registry that can be used to manage subscriptions to the messaging bus for certain data (e.g., data having certain characteristics).

The messaging bus may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Scheduling component 210 includes any suitable computing devices used for business-related purposes with respect to interaction system 200. For example, scheduling component 210 can be configured to schedule a resource for allocation for a particular entity during a particular time slot. Scheduling component 210 can monitor a schedule for the resource and can identify one or more available time slots that may be secured by a particular entity. Upon receiving a scheduling indication, scheduling component 210 may update a schedule of a resource to reflect that a particular time slot is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the data provided by the component or the user device located at the geographic location.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of a same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, have paid a subscription fee associated with access to data store 226, and the like.

Access management engine 222 may also verify that the user device 228 has an IP address or geographical location that corresponds to an authorized list, that the user device 228 includes a plug-in for properly accessing data store 226, that the user device 228 is running certain applications required to access data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized users (e.g., clinical professionals, friends and family members of dependent users, professional users, and/or other suitable authorized users). The information exchange engine 238 is also configured to route inbound messages and route outbound messages, as described herein. The information exchange engine 238 is also configured to generate customized messages based on dependent user data and professional users.

Figure 3:
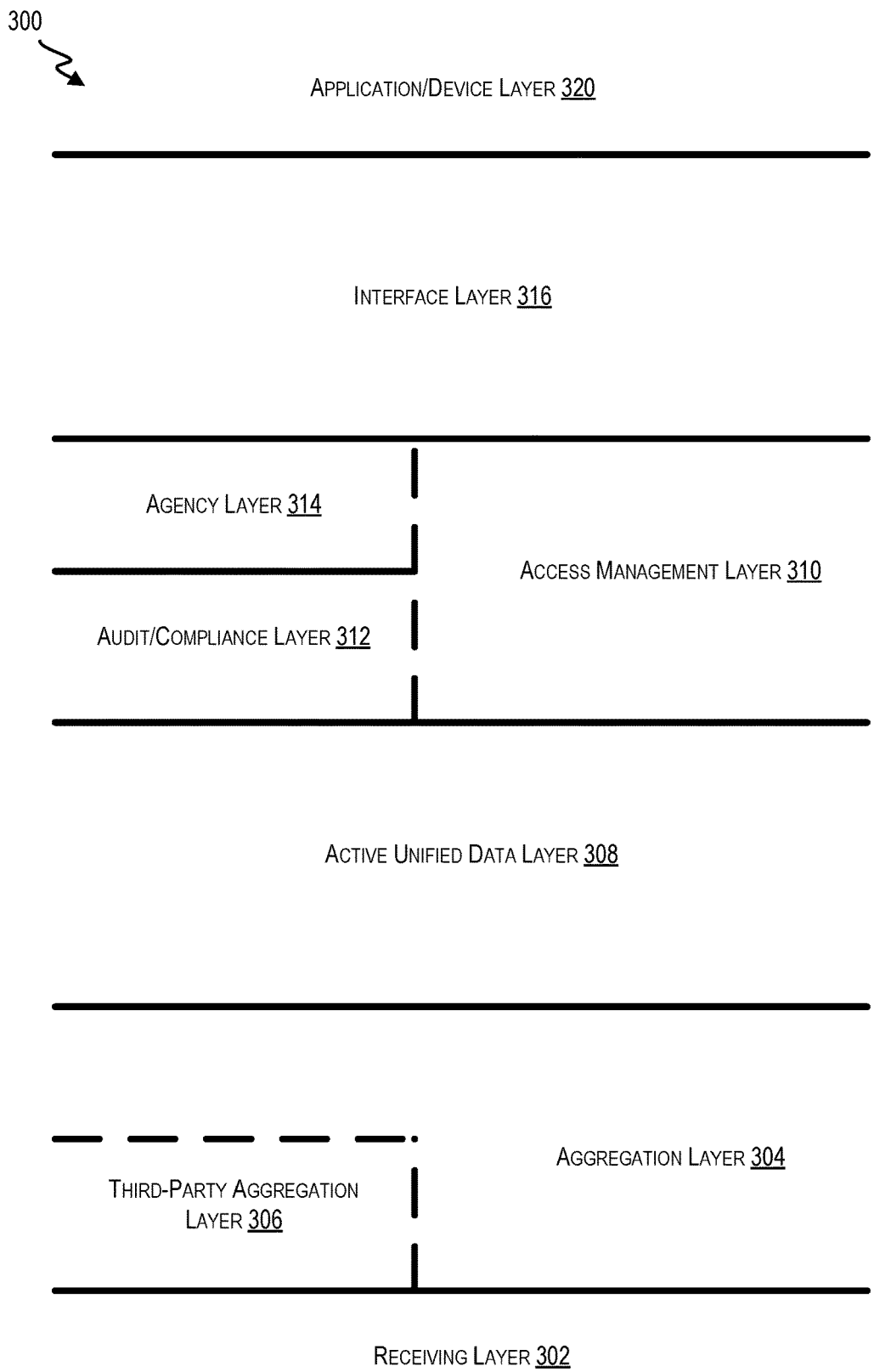
FIG. 3 is an example schematic model illustrating a network communication model in which techniques relating to signal processing for making predictive determinations may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
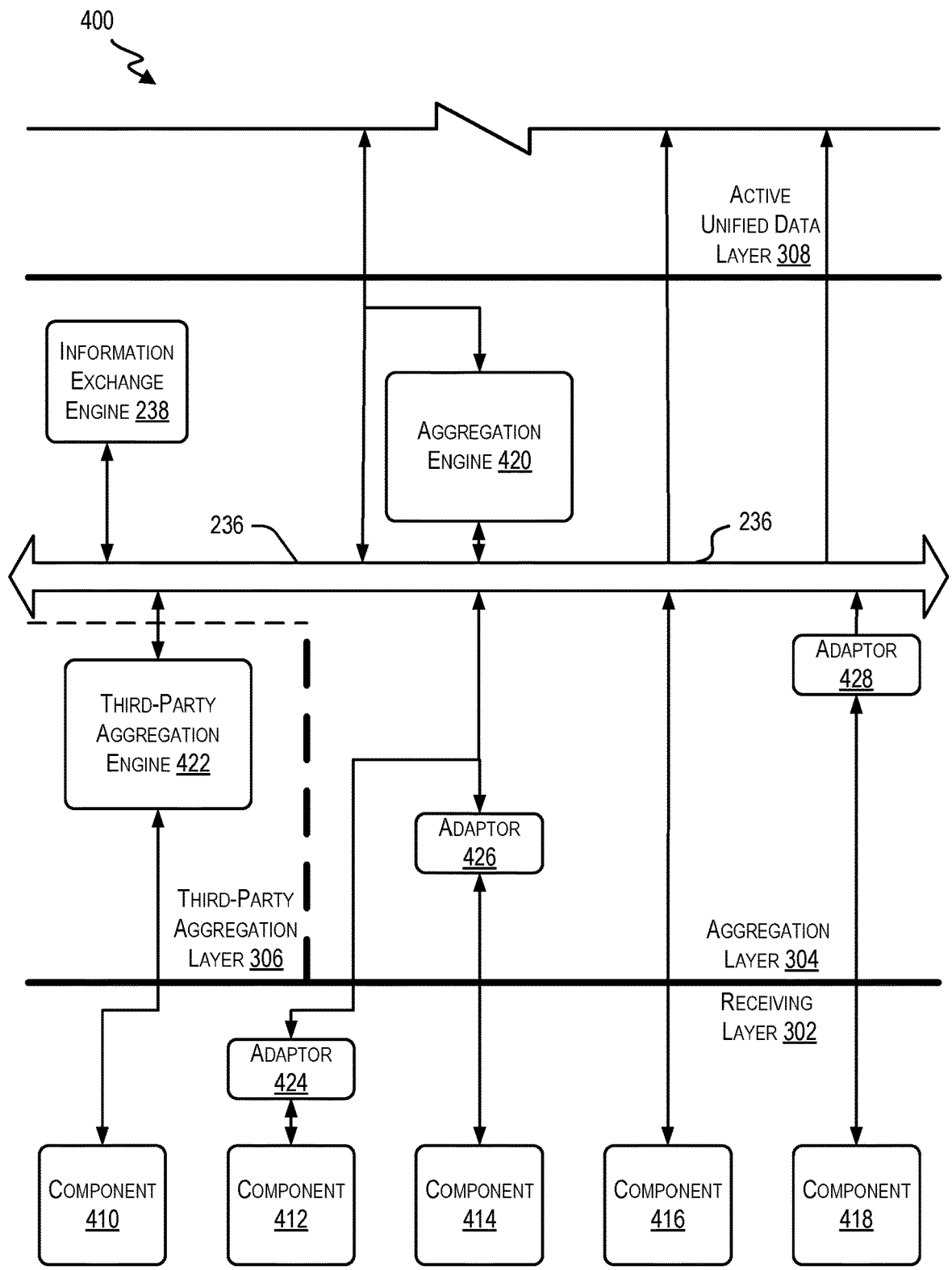
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
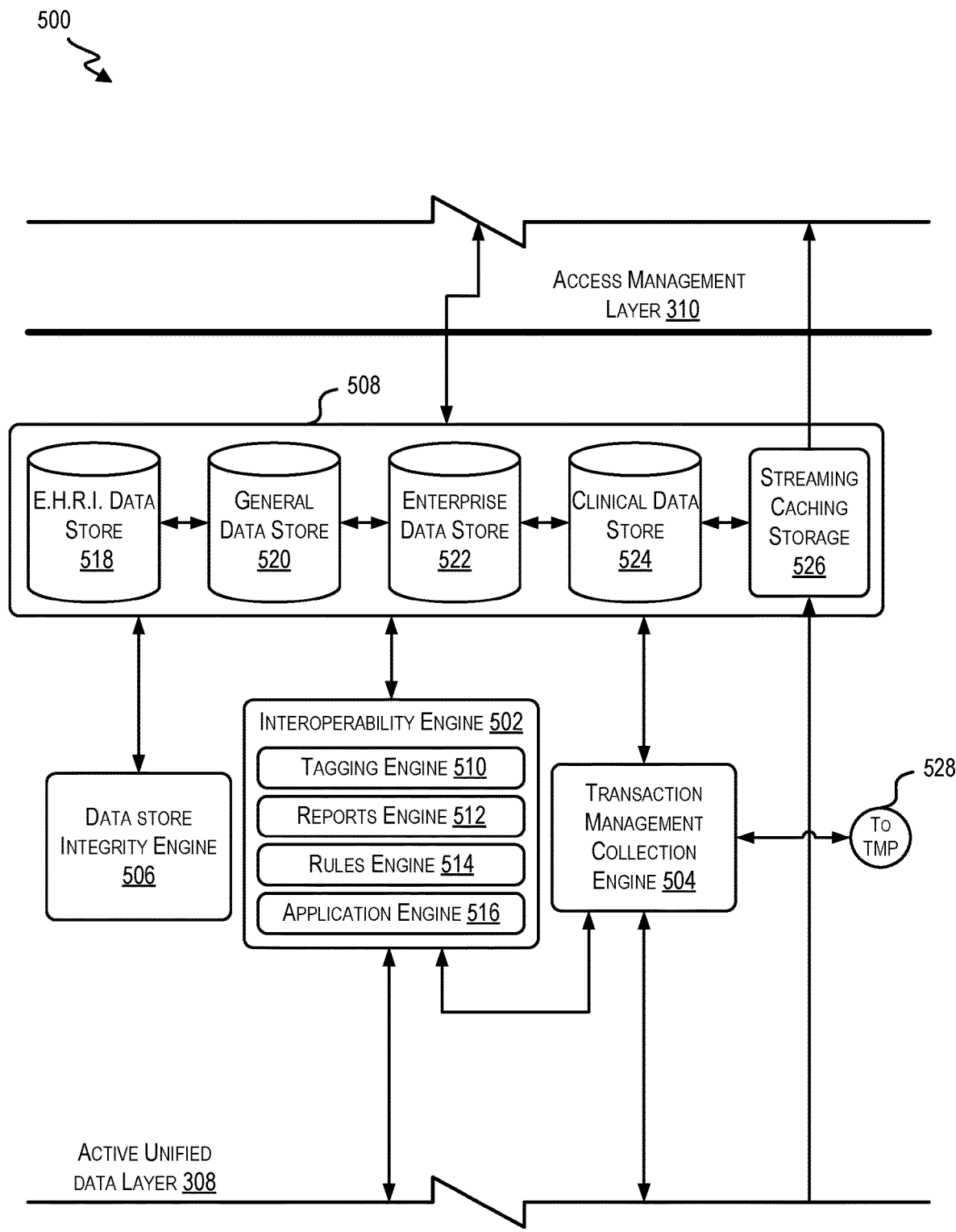
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a transaction management collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Transaction management collection engine 504 is implemented as part of transaction management engine 106. Transaction management collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), transaction management engine 106 (e.g., transaction management collection engine 504 of transaction management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to transaction management engine 106 that it saw the message. In this manner, transaction management engine 106 may enable end-to-end tracking of messages for the life of the message.

In one example, the messages are requests. The requests may be generated based om user input at one of the components. The requests may be received by transformative processing engine 108 and integrated into the system. In some examples, transaction management engine 106 may be notified that the requests have been received and may therefore be configured to generate message IDs for each request. These message IDs may then be associated with each of the requests. As the requests continue to move throughout the interaction system (e.g., away from transformative processing engine 108), transaction management engine 106 may be track their movement using the message IDs. If one of the requests does not make it to its destination, transaction management engine 106 (or part of the transaction management platform 528) may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, transaction management engine 106 (e.g., transaction management collection engine 504 of transaction management engine 106) may receive the message and/or message identifier directly from one of components 410-418. For example, one of components 410-416 may be configured to generate the unique message identifier and/or communicate directly with transaction management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, transaction management collection engine 504 provides unique message identifiers to other elements of the interaction system to monitor the messages as they move throughout the interaction system. Transaction management collection engine 504 also provides a portion of the unique message identifiers to a transaction management platform (indicated by a circle 528) for further analysis of the message identifiers. Such analysis may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage business rules, condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("record data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within record data store 518 is retained data including electronic record information. In some examples, the information within record data store 518 is organized according to entity identifying information. Thus, record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. F2. In some examples, the operational data ware house 522 includes data pertaining to decision making as discussed herein and other data typically used by conventional business concerns.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of personal record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live or substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
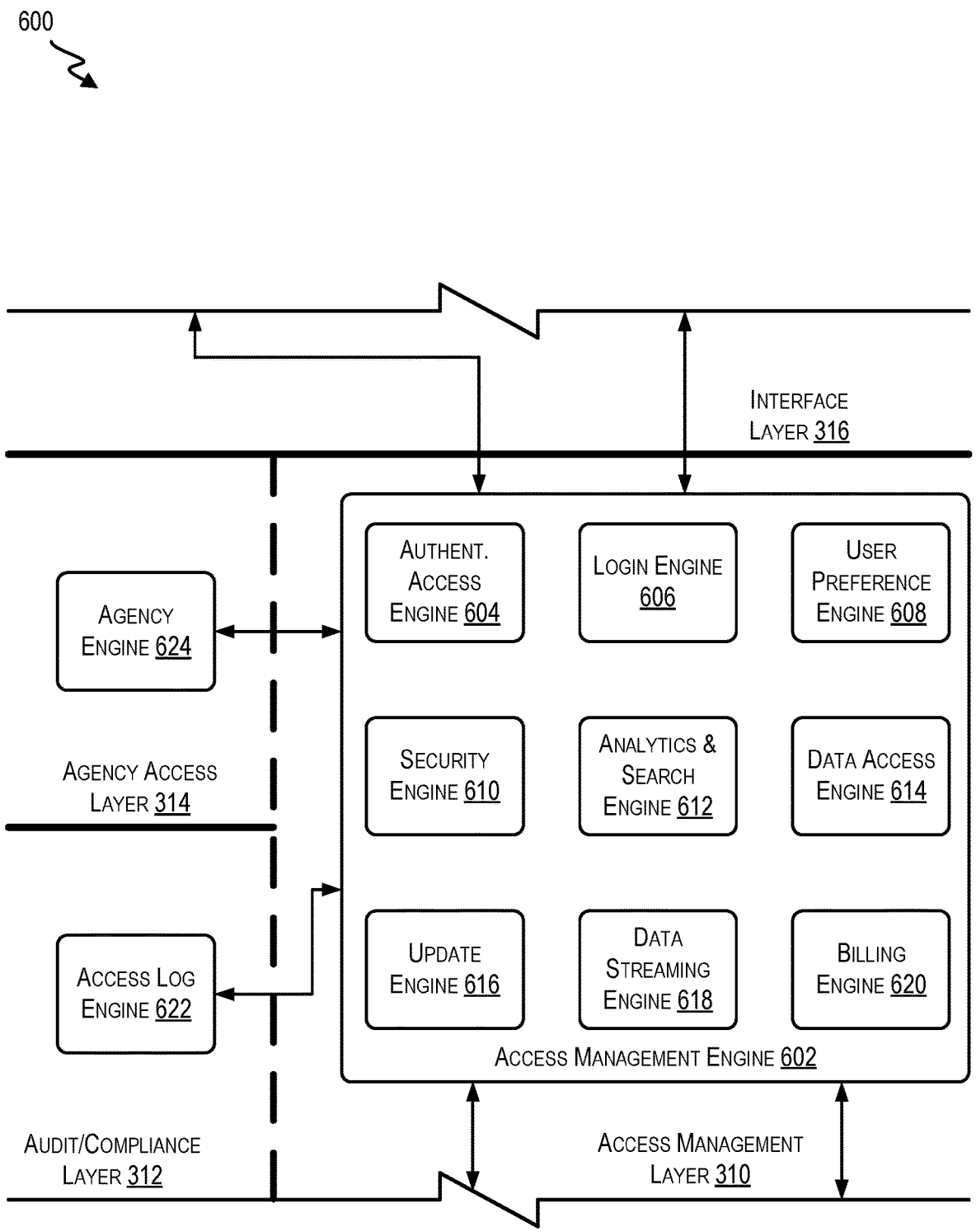
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. For example, agencies that may use agency engine 624 include agencies to which the interaction system provides compliance, tracking, or other reporting information. For example, agency engine 624 may be used to track one or more performance indicators identified by a government agency and/or to provide report instances of defined types of events. Thus, in some examples, a government agency uses agency engine 624 to collect data pertaining to compliance of the interaction system with one or more statutes or regulations. In some examples, a university is an agency that uses agency engine 624 to collect data pertaining to one or more studies. In some examples, agency engine 624 can identify one or more entities (e.g., governmental agencies) that are to receive reports pertaining to operations or events and what types of data are to be reported to those entities. Agency engine 624 can then collect the pertinent data, potentially format and/or analyze the data, and facilitate transmission of (e.g., raw, formatted and/or analysis of) the data to the appropriate agency.

Figure 7:
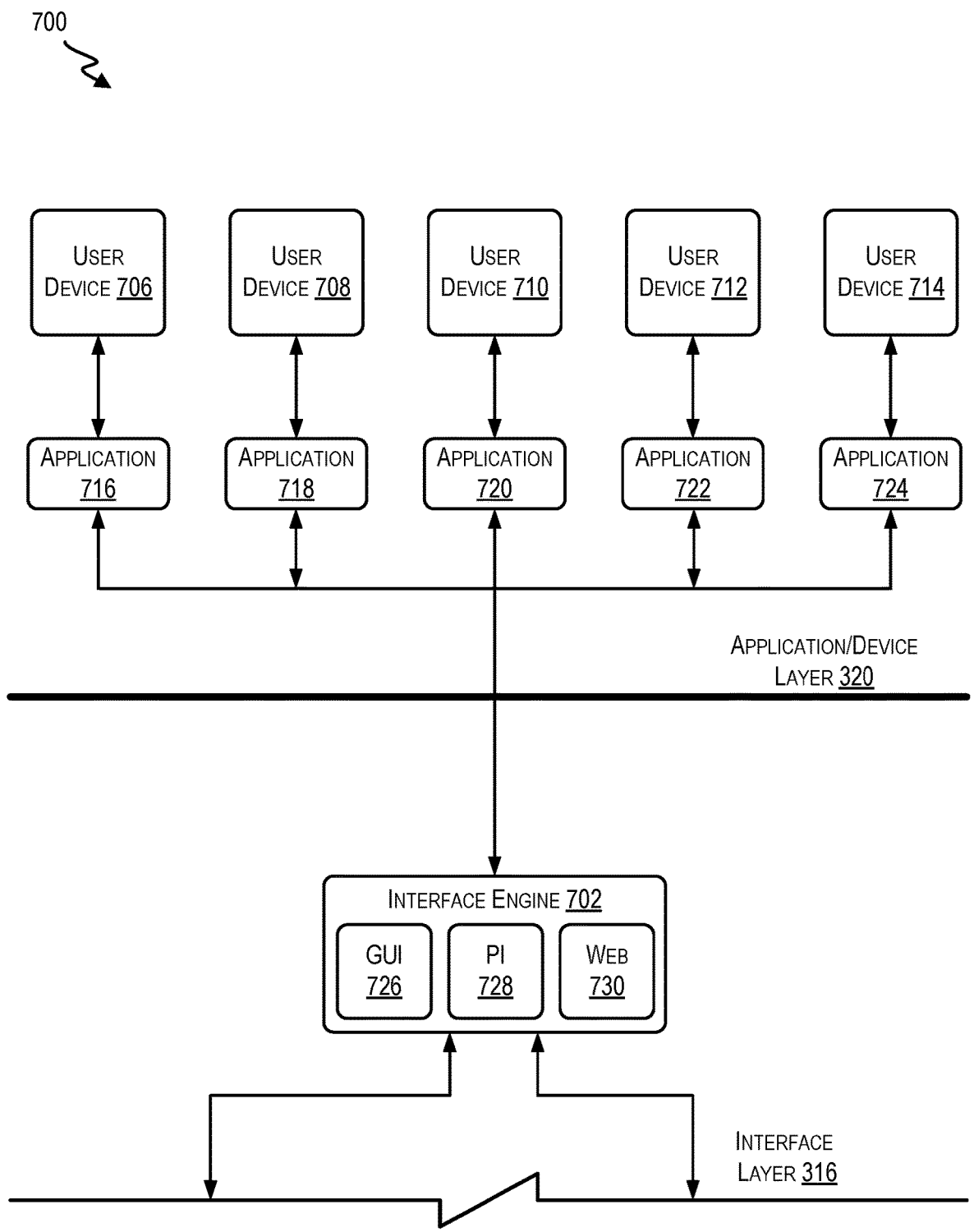
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 716-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for an particular entity. In some examples, application 720 may present different data depending on a specialty associated with the entity and protected information associated with the entity. In this manner, application 720 adapts and automatically adjusts depending on the context in which the entity is using the application. In some examples, the data indicates performance statistics for the entity, metrics relating to where the entity falls along a distribution of other similar entities, outlier instances, trends in events or actions, and the like. Application 720 may be configured to receive input, adjust presentations, present unpromoted alerts, adjust display of content, move more relevant content to the foreground, move less relevant content to the background, populate forms for the entity.

In another example, application 722 may be specific for nurses or types of nurses. In this example, application 722 may include dashboards, widgets, windows, icons, and the like that are customized to individual nurses. Similar to the example discussed above pertaining to the authorized user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

In some examples, application 724 may be a business intelligence application. In this example, application 724 is used to display business information generated by components of the interaction system. This business information can be used for operations, planning, and forecasting. Such business information may include data because such data may impact operations, planning, forecasting, and the like. Accordingly, application 724 may present de-identified information in the form of one or more metrics, indicators, or the like as they pertain to business intelligence.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
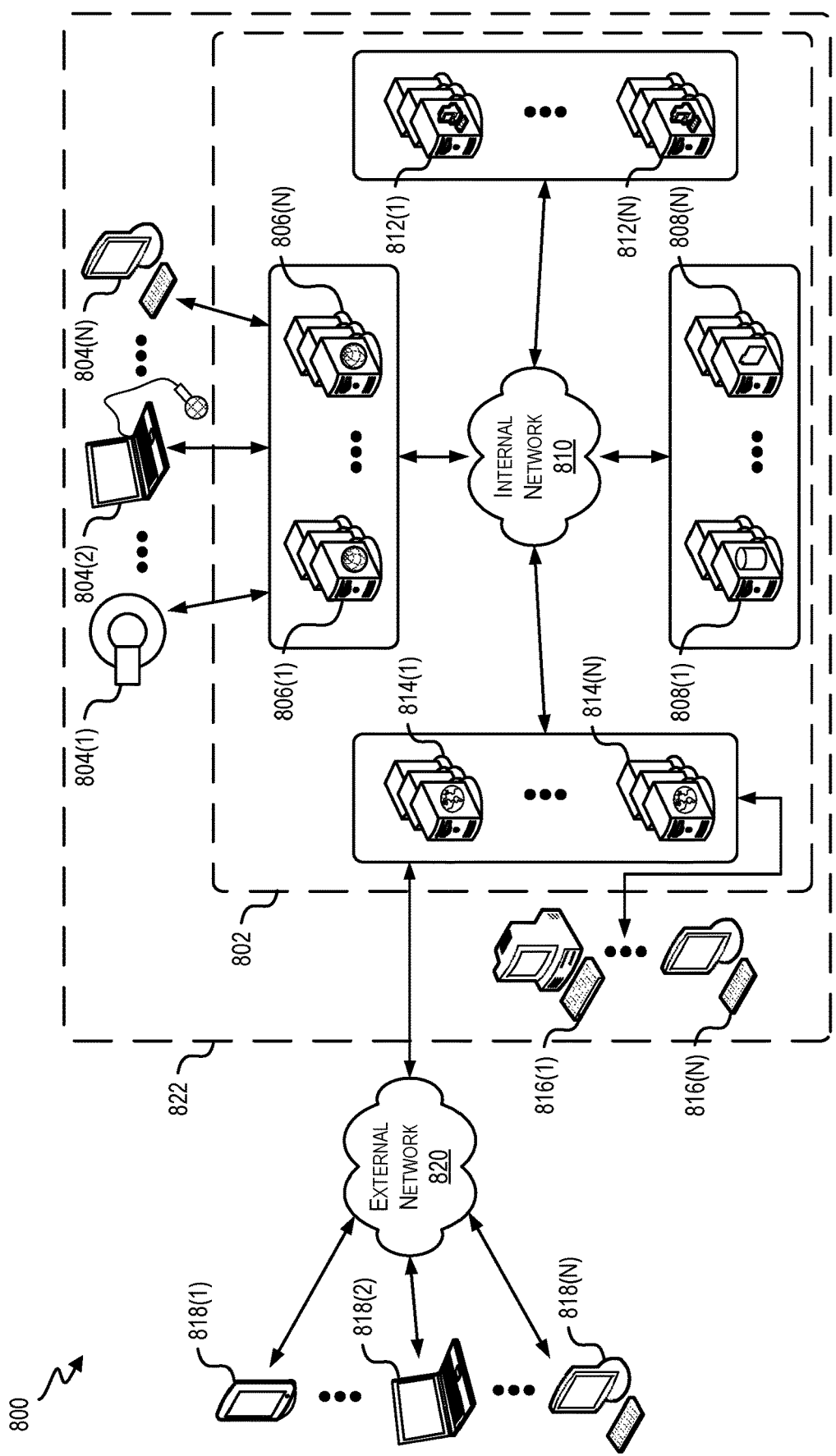
FIG. 8 is an example schematic architecture illustrating an interaction system in which techniques relating to signal processing for making predictive determinations may be implemented, according to at least one example.

Turning now to FIG. 8, an interaction system 800 is shown, according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

The systems, environments, devices, components, models, and the like of FIGS. 1-8 may be used to implement a particular system as described herein and additionally described in U.S. application Ser. No. 15/299,324 filed Oct. 20, 2016; U.S. Application No. 62/244,645 filed Oct. 21, 2015; U.S. application Ser. No. 16/450,314 filed Jun. 24, 2019; U.S. application Ser. No. 15/829,733 filed Dec. 1, 2017; and U.S. Application No. 62/428,911 filed Dec. 1, 2016; the entire contents of each of the above-referenced applications are hereby incorporated by reference for all purposes. In one example, a predictive condition engine is provided. Generally, the predictive condition engine accesses certain data signals and attempts to predict whether a dependent user (e.g., a patient) has developed or is likely to develop a particular condition. In a particular example, the predictive condition engine can be used to determine a likelihood that a dependent user has or will develop a particular clinical condition such as a cellular abnormality (e.g., cancer or other cellular abnormality) or other non-cellular abnormalities. It is understood that the techniques described herein are not limited to cellular abnormalities, and can therefore be implemented to determine likelihoods for conditions other than cellular abnormalities. Given the high mortality rate for dependent users who are determined to have cellular abnormalities, identifying early signs of these abnormalities and alerting the correct authorized users (e.g., clinical professionals) may enable these authorized users to take certain steps to prevent negative outcomes, including death. To this end, the predictive condition engine is configured to identify early signs that a dependent user has developed or is on a path to developing one or more cellular abnormalities, and to notify an appropriate authorized user using an appropriate method.

To this end, the predictive condition engine accesses messages including notes (e.g., medical notes) prepared by authorized users and other unstructured data signals prepared on behalf of the dependent user or captured in relation to the dependent user. These unstructured data signals may include descriptions of aspects of the dependent user's conditions not capable of being adequately represented by objective, structured data. In some examples, these description may be referred to as "sentiments" of the authors of the unstructured data signals. For example, in a note, an authorized user can include her impressions about the dependent user's condition, the dependent user's mood, the dependent user's responsiveness, the dependent user's attitude, and any other descriptions that relate to the condition of the dependent user. The predictive condition engine accesses such unstructured data signals in about real time. This includes, for example, accessing a stream of data originating from a system in which the authorized users' notes about the dependent user are entered. For example, a stream from a certain system (e.g., electronic record service, specialized medical devices or equipment, etc.) of care organization network in real-time can be accessed. The predictive condition engine evaluates a portion of the unstructured data using a natural language processing predictive model to extract subjective indicators from the unstructured data. From these indicators, the predictive condition engine uses a predictive model based on machine learning techniques to predict whether the dependent user has the condition or is likely to develop the condition. The natural language processing model can be trained on a corpus of unstructured data (e.g., authorized users' notes, dependent user-prepared materials, and the like) prepared by various individuals and identifying at least some dependent users that developed the relevant condition. The natural language processing model is thus trained to identify assessments, plans, or sentiments in the unstructured data. In some examples, a subject assessment score determined based the subjective indicators may indicate a likelihood that the dependent user has or will develop the condition within a particular time period. The time period can be determined based on the results of the analysis described herein.

In addition, the predictive condition engine evaluates the notes (or other free form text) and extracts other data in a semantically meaningful way from the notes. This data, in this example, can include elements of the text such as words, numbers, order of words with respect to other words, sentence syntax, paragraph syntax, spacing between words, misspellings, grammatical mistakes, and any other element of the text. Extracting the data in a semantically meaningful way can include identifying relationships between the elements that have been extracted and storing these relationship. These relationships can be compared to relationships identified previously from other notes describing dependent users having similar conditions. These other relationships can be stored in the predictive model. In this manner, the data extracted from notes can also be used to generate a report about the condition.

As an additional part of identifying conditions of dependent users, the predictive condition engine accesses an electronic record of the dependent user. The electronic record will typically include lab values, vital sign readings, and other objective data. These objective data may be considered structured data. The predictive condition engine evaluates a portion of the electronic record; in particular, a portion of the objective data that can be used by a predictive model to generate an objective assessment score for the dependent user. The predictive model can be based on records for dependent user populations that ultimately were assigned the condition. In some examples, the objective assessment score indicates a likelihood that the dependent user has the condition or will develop the condition within a certain period of time. The predictive condition engine uses the subject assessment score and the objective assessment score to determine a composite assessment score indicating an overall likelihood. The objective assessment score, the subjective assessment score, the composite assessment score, and/or any other relevant output from the predictive condition engine can be provided to a routing engine. The routing engine includes rules to determine whom to send the output. Once an appropriate entity, person, or machine is identified, the routing engine causes the output to be delivered.

Use of the predictive condition engine improves the functioning of the computer system in which the predictive condition engine is implemented. Because the predictive condition engine monitors existing digital messages and does not add traffic to the network, the techniques described herein are implemented without affecting existing bandwidth constraints. Moreover, because the natural language processing models and predictive models are trained using the largest and most relevant datasets available (i.e., those maintained in an enormous clinical data warehouse), the predictions made using the described system are more precise and more accurate than those made by prior art systems trained using corpuses of generic text. Additionally, because of the quality of the models, fewer computing resources are required to make the predictions as would be required using the prior art systems.

Examples of the disclosure provide for a number of technical advantages. For example, the disclosure enables operators of medical networks to offer better customization for their authorized users and for their dependent users, resulting in improved and contextualized care. By implementing the techniques described herein on a centralized server, processing capabilities are freed up on local computing devices. Such centralization also improves the accuracy and precision of the predictive models described herein. For example, because all or almost all messages flow from record service end points through the centralized server (e.g., via integration), the predictive models can continuously be updated based on the messages.

Figure 9:
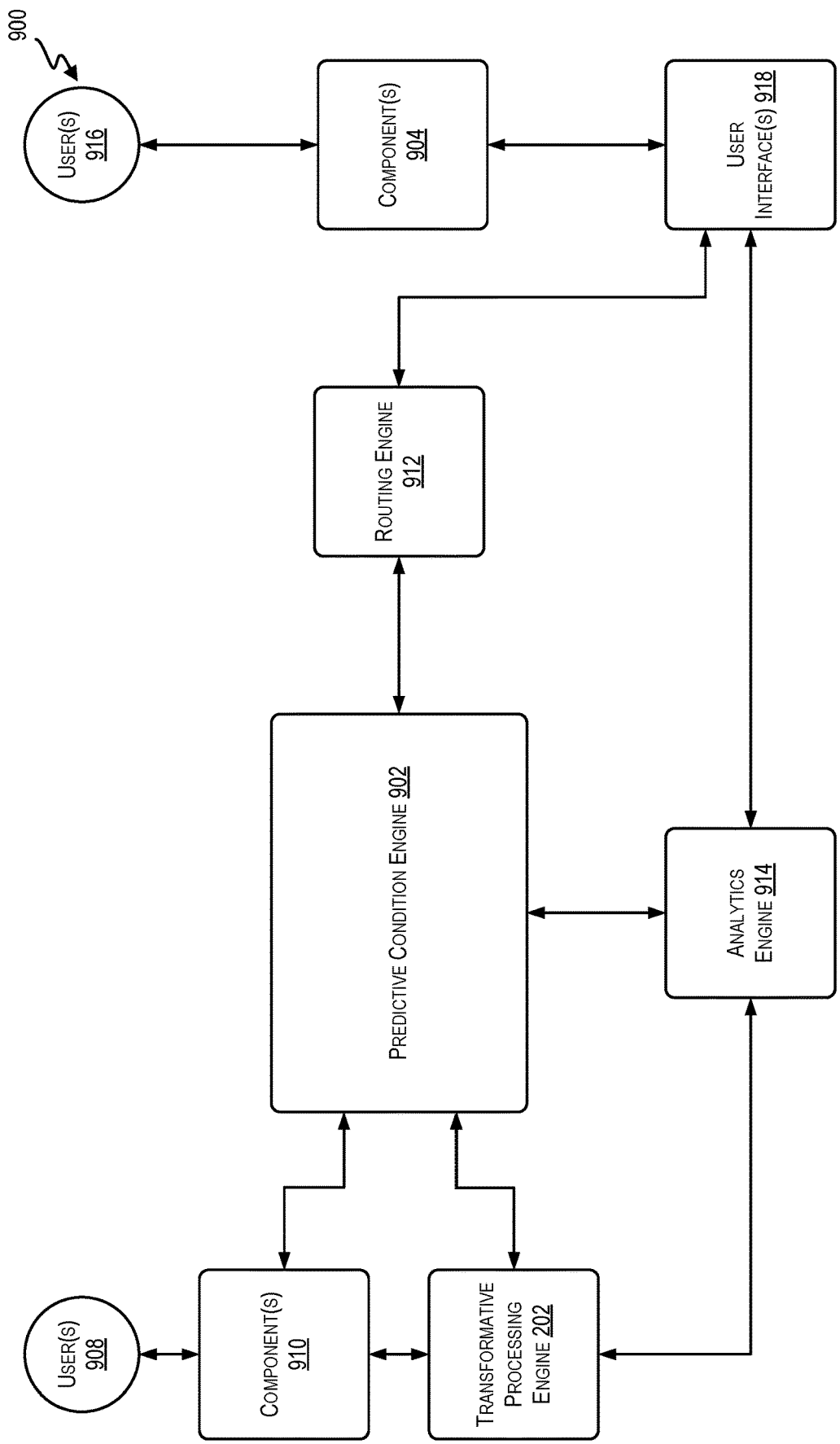
FIG. 9 is an example block diagram illustrating an interaction system in which techniques relating to signal processing for making predictive determinations may be implemented, according to at least one example.

Turning now to FIG. 9, an interaction system 900 is shown according to at least one example. The interaction system 900 may be implemented using at least some of the elements of FIGS. 1-8. In this manner, the interaction system 900 includes computer components (e.g., personal electronic devices, servers, virtual machine instances, specialized equipment, specialized diagnostic and treatment devices, and/or other similar computer components) communicatively coupled via one or more communication networks. The interaction system 900 includes a predictive condition engine 902, which is configured to implement the techniques described herein. For example, the predictive condition engine 902 generates decision support output (e.g., condition reports, predictions, deterioration status, and the like) that can be provided to a routing engine 912 to determine appropriate receiving users 916, who can view the decision support output via at one or more components 904 using one of more user interfaces 918. In a particular example, the predictive condition engine 902 is configured to evaluate unstructured data signals and/or structured data signals to predict whether a particular condition is present in a dependent user, whether the dependent user is at risk for the particular condition, and other similar determinations. To this end, the predictive condition engine 902 can generate scores based on the evaluation of the structured and/or unstructured data signals. These scores may indicate a correspondence between the particular condition and the data signals. The predictive condition engine 902 may use the scores to generate reports, which can be shared with one or more authorized users. For example, the authorized user who is responsible for some aspect of the health of the dependent user can get the reports.

In some examples, output from the predictive condition engine 902 may be a deterioration profile that may include one or more scores. In some examples, the output from the predictive condition engine 902 may be a plan for contacting a dependent user to schedule one or more follow-up appointments and may be provided to a contact center entity to schedule the appointments.

In order to generate its particular class of decision support output, the predictive condition engine 902 is configured to receive and analyze data. The particular data that the predictive condition engine 902 analyzes may be different depending on the circumstances surrounding the dependent user. In addition, the predictive condition engine 902 may analyze data using different language processing models and predictive models, which may be trained on data that is specific to type of data being analyzed.

In some examples, the data that can be analyzed by the predictive condition engine 902 includes note data (e.g., notes from authorized users who have different roles with respect to the dependent user, dependent user-prepared materials, transcriptions of notes, recordings (or transcriptions) of interactions between dependent users and authorized users and/or between dependent users and others (e.g., family members), notes regarding eating habits of a dependent user, notes regarding bathroom habits of the dependent user, prescription notes, release notes (e.g., emergency room release), notes regarding radiology and other tests, and other types of subject data) and objective data (e.g., orders, lab results, vital signs from chart, objective output from devices and/or systems, pharmacy orders, weather conditions, and other types of objective data). In some examples, the note data includes unstructured data (e.g., letters, numbers, and symbols stored in an unknown format) and the objective data includes structured data (e.g., letters, numbers, and symbols stored in a known format). However, the structured data may also include some subjective data and the unstructured data may include some objective data. Other forms of data, which may be structured or unstructured, include, for example, raw data outputs from equipment or devices (e.g., waveform data, alarms, images, signal data, settings on machine, etc.), sensors of various types within a dependent user's room (e.g., a sensor that indicates movement of the dependent user on a dependent user bed, a sensor that indicates interaction of the dependent user with an audio/video system in the room, a sensor that indicates interaction with lights in the room, a sensor that indicates interaction with bathroom appliances, a sensor that indicates interactions with a climate control in the room, a sensor that indicates interactions with window shades in the room, a sensor that indicates information provided on a digital whiteboard in the room, a sensor that indicates interaction with personal electronic devices in the room, a sensor that collects audio and/or video of interactions within the room, and any other suitable sensor) sensors to track movement of the dependent user within the facility (e.g., radio-frequency identification RFID sensors and readers), any other suitable sensors, metadata in communications regarding the dependent user (e.g., number of messages sent, how often, to whom, at what time, and any other suitable information that may be retained as metadata), and any other suitable unstructured data or live stream data.

The creation of data begins with generation users 908. Use of decision support output is utilized by receiving users 916 via user interfaces 918. The generation users 908 and the receiving users 916 may come from the same group of users and may be similar to the users that operate the components 410-418 and/or the users that operate the user devices 706-714, as described herein. Accordingly, the generation users 908 interact with components 910 to generate data, and the receiving users 916 receive decision support output via the user interfaces 918. In some examples, the user interfaces 918 are implemented at one or more of the components 910. In other words, a particular component 910 can generate data and can also receive decision support output. The components 910 and the components 904 are examples of the components 410-418 discussed herein. Thus, in some examples, the components 910 automatically generate data without input by the generation users 908. For example, an automated process running on a particular component 910 periodically outputs a report of current dependent users. In some examples, the components 910 are used by the generation users 908 to input data about the dependent users. For example, the generation users 908, which may be authorized users, may prepare observations in the form of notes about visits with the dependent users. These notes can be transferred as messages.

The routing engine 912 is configured to determine appropriate users out of the receiving users 916 and/or an appropriate user interface out of the user interfaces 918 to which the decision support output should be sent. In some examples, the routing engine 912 includes a plurality of rule sets which define the conditions under which a message, including a contextual report, will be sent to a particular recipient. To this end, decision support output from the predictive condition engine 902 is provided to the routing engine 912, and the routing engine 912 determines to whom and, in some cases, what of the decision support output to send. The decision support output can be provided directly to the user interfaces 918 to be consumed by the receiving users 916 using the components 904.

An analytics engine 914 is configured to evaluate decision support output generated by the predictive condition engine 902. This includes, for example, determining precision, accuracy, false-discovery-rate, false-negative-rate, fall-out, recall, specificity, negative-predictive-value, and/or any other suitable metric for tracking aspects of the predictive condition engine 902. In some examples, the analytics engine 914 evaluates the models supported by the predictive condition engine 902 based on notes from the corpus of text used to train the models. In some examples, the analytics engine 914 evaluates the models supported by the predictive condition engine 902 by evaluating an ultimate outcome based on a new note. In some examples, the analytics engine 914 evaluates outcomes and/or results in accordance with other metrics, which may be qualitative or quantitative.

Figure 10:
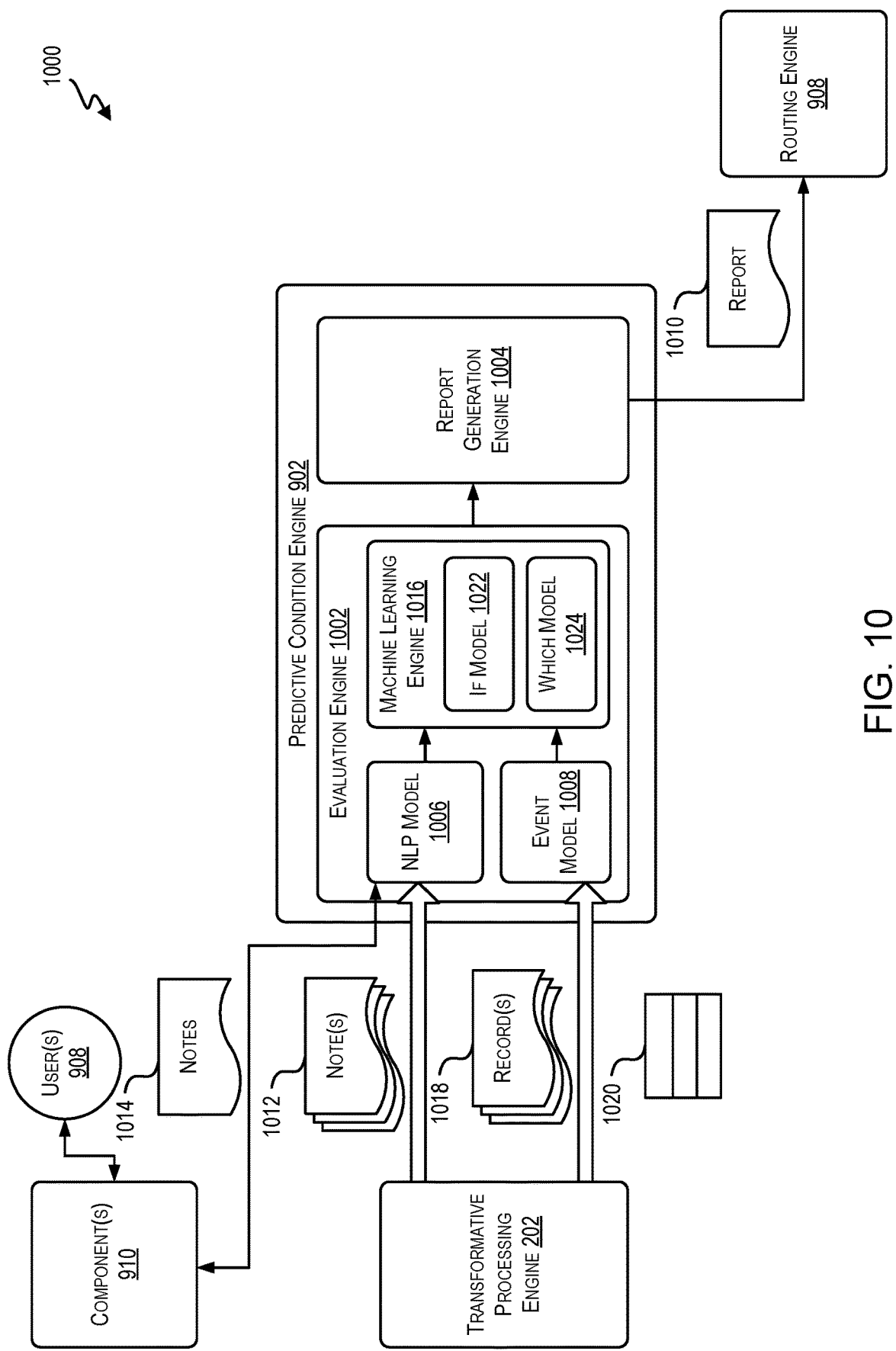
FIG. 10 is an example block diagram illustrating an interaction system in which techniques relating to signal processing for making predictive determinations may be implemented, according to at least one example.

Turning now to FIG. 10, an interaction system 1000 is shown according to at least one example. The interaction system 1000 includes the predictive condition engine 902 in communication with the components 910, the transformative processing engine 202, and the routing engine 912. The predictive condition engine 902, in this example, includes an evaluation engine 1002 and a report generation engine 1004. Other example configurations of the predictive condition engine 902 are described herein with reference to other figures. The evaluation engine 1002 is configured to manage operation of one or more models including, for example, a natural-language processing (NLP) model 1006 and an event model 1008. The evaluation engine 1002 is also configured to manage the operation of a machine learning engine 1016, which includes its own models. The report generation engine 1004 is configured to evaluate output from the evaluation engine 1002 in order to determine a condition report 1010 (e.g., a cellular abnormality report). The condition report 1010 can be based on separate assessment scores derived from output from the NLP model 1006 and from output from the event model 1008, as processed by the machine learning engine 1016. In this manner, the condition report 1010 can include a composite score based on the assessment scores from the two models 1006, 1008. In some examples, the NLP model 1006, the event model 1008, and the machine learning engine 1016 are included as part of one device and/or distributed among more than one device. In some examples, the function of the NLP model 1006, the event model 1008, and the machine learning engine 1016 may be distributed among a structured data evaluation engine 1104 and an unstructured data evaluation engine 1106 described with reference to FIG. 11.

The NLP model 1006 is a data extraction model that is implemented using natural-language processing techniques. Depending on the implementation, the NLP model 1006 can be trained on a corpus of unstructured data that includes at least a plurality of notes 1012. The plurality of notes 1012 are notes that may be associated with dependent user records stored under the management of the transformative processing engine 202. In some examples, the plurality of notes 1012 are organized or accessible based on a condition either explicitly addressed in the notes 1012 or that dependent users to which the notes 1012 belong ultimately developed. For example, if the condition being evaluated by the predictive condition engine 902 is a cellular abnormality, the plurality of notes 1012 that are used to train the NLP model 1006 are those notes that correspond to the cellular abnormality. In this manner, the NLP model 1006 is trained using relevant notes that described or were otherwise associated with the topic of the cellular abnormality.

The NLP model 1006 can be tested as part of its training. This includes, for example, evaluating certain notes of dependent users known to have developed the cellular abnormality, to see if the NLP model 1006, in connection with the machine learning engine 1016, can correctly detect the presence of the cellular abnormality. Training the NLP model 1006 may include adjusting one of a number of parameters which are used to identify relationships between, first, certain unstructured data within notes language nuances, and second, outcomes for a particular condition.

In some examples, the NLP model 1006 is configured to parse a set of dependent user notes 1014 that are provided to the evaluation engine 1002 from the components 910. For example, the evaluation engine 1002 may access a stream of messages including dependent user notes (or other messages) including the set of dependent user notes 1014. In some examples, a first component 910 (e.g., a computer in a hospital) is used to generate one or more of the set of dependent user notes 1014 which are sent to a second component 910 (e.g., an electronic record storage service) in the form of a standardized message (e.g., HL7 message) for storage. In some examples, the evaluation engine 1002 accesses the set of dependent user notes 1014 as they are being sent from the first component 910 to the second component 910 for storage. In some examples, the evaluation engine 1002 receives the set of dependent user notes 1014 directly from one of the components 910. In either example, the evaluation engine 1002 may access the set of dependent user notes 1014 in about real time, i.e., as they are being prepared or shortly afterwards. For example, a recording device, which is an example of one of the components 910 can be used by an authorized user, who is an example of one of the generation users 908, to record a dependent user note. The recording of the authorized user's voice describing the dependent user's condition can be received by the evaluation engine 1002 and evaluated by the NLP model 1006. Of course a transcribed copy of the voice recording or a prepared note may also be received by the evaluation engine 1002.

The set of dependent user notes 1014 include notes similar to the plurality of notes 1012 that were used to train the NLP model 1006. In some examples, the set of dependent user notes 1014 include prose text that is unstructured and that describe conditions of a dependent user. In certain arrangements, dependent user notes 1014 are prepared by authorized users such as clinical professionals and others who interact with the dependent user. In some examples, the dependent user notes 1014 are prepared by specialists who are trained to identify certain conditions. In some examples, the dependent user notes 1014 may be one of a variety of note types. Examples of note types may include, for example, lab notes, visit notes, medication notes, report notes, and any other suitable note type.

The dependent user notes 1014 may be prepared by authorized users at a shift change, periodically (e.g., every hour), and at any other suitable interval. In some examples, the set of dependent user notes 1014 are prepared in accordance with a standard format. For example, a section devoted to treatments administered to the dependent user, a section devoted to drugs administered, a section devoted to statements of the dependent user, a section devoted to directions given to the dependent user, a section devoted to general impressions about the dependent user's health, and any other format. In some examples, the NLP model 1006 uses the standard format as part of evaluating the set of dependent user notes 1014. In some examples, the set of dependent user notes 1014 are prepared without regard to a standard format.

In some examples, the set of dependent user notes 1014 include a preparer's (e.g., an authorized user or other example generation user 908) subjective observations, impressions, and concerns about the health of the dependent user. These may be conveyed by the preparer's choice of language nuances. These nuances, include for example, use of direct or passive voice, tone, sentiment, humor, sarcasm, word choice, sentence structure, grammatical structure, and other forms of speech which are commonly used by writers. In some examples, a human reading the set of dependent user notes 1014 may be able to understand these subjective observations, impressions, and concerns of the preparer. A human that is familiar with the writing style of the preparer may be even better equipped to understand these subjective observations, impressions, and concerns, collectively, e.g., subjective indicators. In some examples, the evaluation engine 1002, in particular the NLP model 1006, is configured to evaluate the set of dependent user notes 1014 to understand these subjective observations, impressions, and concerns in a manner that is faster, more efficient, more robust, and more accurate than could be performed by a single human (or many humans).

As part of parsing or otherwise evaluating the set of dependent user notes 1014 introduced above, the NLP model 1006 selects a hypothetical outcome for a particular condition (e.g., dependent user X has a cellular abnormality) and evaluates the set of dependent user notes 1014 to identify subjective indicators such as words, relationships between words, meaning, sentiment, tone, observations, impressions, concerns, and the like that support the hypothetical outcome. In some examples, this output can be characterized as a set of facts (e.g., people, places, things, times, dates, etc.) in a structured format that can be provided to the machine learning engine 1016 for further evaluation.

The machine learning engine 1016 may include any suitable combination of machine learning algorithms and/or models such as an if model 1022 and a which model 1024 in order to evaluate the set of facts. This includes assigning weight values to the identified subjective indicators based on a relevance of the subjective indicator alone to the cellular abnormality and the subjective indicator with respect to other subjective indicators. In some examples, the machine learning engine 1016 generates a prediction of whether the dependent user indeed has the condition or is deteriorating toward the condition. In some examples, the prediction is provided in terms of score indicating a likelihood that the dependent user has the condition or is deteriorating toward the condition, i.e., is likely to develop the condition. The prediction, including any assessment scores, can be provided to the report generation engine 1004 to generate the condition report 1010. In some examples, the report generation engine 1004 includes functionality to generate an assessment score from output from the machine learning engine 1016.

For some conditions such as cellular abnormalities, there may be many different condition types. The treatment options, survival rates, and the like are various for the different condition types. Thus, it may be desirable to not only determine if the dependent user has the condition, but to also determine which condition of a plurality of conditions the dependent user likely has. To this end, the which model 1024 is provided as part of the machine learning engine 1016. The which model 1024 is used to determine which condition from a set of conditions that was identified by the if model 1022. This additional information (e.g., which condition) can be used to tailor contact plans, response plans, and reports relating to treatment. As described herein, the which model 1024 may also rely on the subjective indicators and the relationships between the identified subjective indicators. In some examples, each possible condition from the set of conditions may be assigned a condition score based on evaluation of the notes. The which model 1024 may rely on a set of rules such as threshold rules to which the condition scores can be compared to determine whether the dependent user "has" the particular condition.

Like the NLP model 1006, the event model 1008 is a predictive model. The event model 1008, however, is implemented to make predictions based primarily on structured data accessed from the transformative processing engine 202. In some examples, the event model 1008 accesses structured data that is stored in one of the database within the data store 226. In any event, the event model 1008 can be trained on a corpus of structured data that includes at least a plurality of records 1018 stored under the management of the transformative processing engine 202. Like the NLP model 1006, the event model 1008 can be trained on records 1018 that are indicative of a particular condition. For example, if the condition being evaluated by the predictive condition engine 902 is a cellular abnormality, the plurality of records 1018 that are used to train the event model 1008 are those records that correspond to cellular abnormality. In this manner, the event model 1008 is trained using relevant records. In some examples, certain portions of the records 1018 are used to train the event model 1008, while other portions are not used. For example, certain data related to vital sign measurements, lab reports, and the like may be accessed from the transformative processing engine 202 in order to train the event model 1008, while notes within the plurality of records 1018 may not be used.

The event model 1008 is configured to receive and/or access dependent user structured data 1020 from the transformative processing engine 202. The dependent user structured data 1020 is structured data that is specific to the dependent user being evaluated by the evaluation engine 1002. For example, this may a dependent user who is admitted to a hospital and has a likelihood of developing cellular abnormality. In some examples, the techniques described herein are implemented for all admitted dependent users, groups of dependent users (e.g., all post-op dependent users, dependent users over 65, etc.), dependent users with particular conditions, or for any other relevant grouping.

The event model 1008 evaluates the dependent user structured data 1020 in accordance with one or more parameters to determine whether the dependent user has or is likely to develop a certain condition (e.g., a cellular abnormality). In some examples, the event model 1008 outputs an assessment that indicates a likelihood that the dependent user has or is likely to develop the condition. In some examples, the event model 1008 provides some output, and the report generation engine 1004 generates an assessment based on the output.

The report generation engine 1004 is configured to generate the condition report 1010 relating to the dependent user and identifying one or more conditions. In some examples, the condition report 1010 is a composite assessment that is based on an assessment based on the machine learning engine 1016 and an assessment based on the event model 1008. In some examples, each of the assessments includes a score that indicates a likelihood that the dependent user has or will develop the condition. In some examples, the condition report 1010 includes a composite score that is determined based at least in part on the two assessment scores. The condition report 1010 is provided to a routing engine 912 that determines whom to send the condition report 1010.

Figure 11:
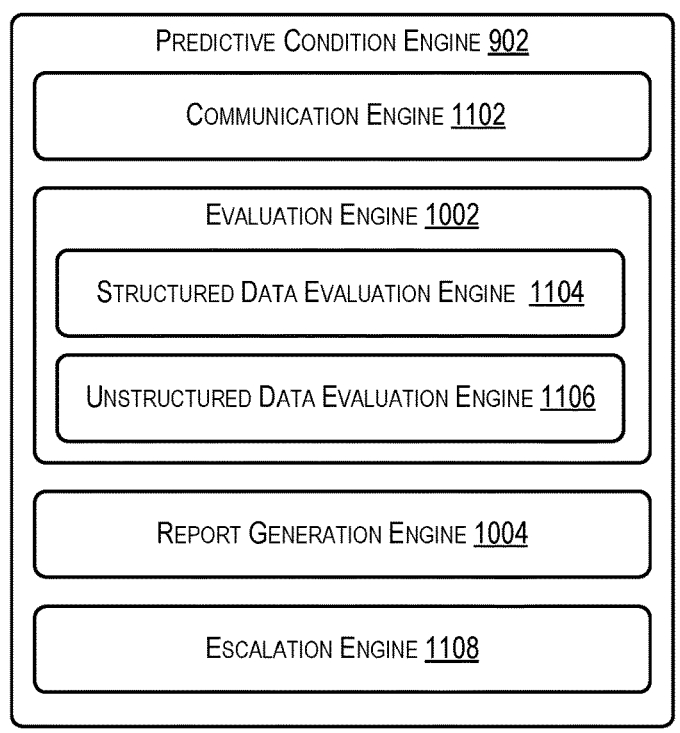
FIG. 11 is an example device which can be used to implement techniques relating to signal processing for making predictive determinations, according to at least one example.

FIG. 11 illustrates an example device 1100 including the predictive condition engine 902, according to at least one example. The predictive condition engine 902 is configured to manage one or more sub-modules, components, engines, and/or services directed to examples disclosed herein. In some examples, the predictive condition engine 902 includes a communication engine 1102, the evaluation engine 1002 (including a structured data evaluation engine 1104 and an unstructured data evaluation engine 1106), the report generation engine 1004, and an escalation engine 1108. While these engines are illustrated in FIG. 11 and will be described as performing discrete tasks with reference to the flow charts, it is understood that FIG. 11 illustrates example configurations and other configurations performing other tasks and/or similar tasks as those described herein may be implemented according to the techniques described herein.

The communication engine 1102 is configured to enable communication with other elements of the interaction systems described herein (e.g., the transformative processing engine 202, the analytics engine 914, the components 910, etc.). In some examples, the communication engine 1102 enables communication between other engines of the predictive condition engine 902. The communication engine 1102 is also configured to enable communication with one or more components and one or more users, whether via the routing engine 912 or otherwise. Thus, in some examples, once a condition report is generated, the communication engine 1102 provides it to the routing engine 912 for appropriate routing. In some examples, the communication engine 1102 determines an appropriate user, user device, and/or user interface to where the report should be sent. In some examples, another component (e.g., the escalation engine 1108) is used to determine the appropriate user, user device, and/or user interface.

The evaluation engine 1002 is configured to monitor, collect, receive, and evaluate data signals such that a condition report for a dependent user can be generated. As described with reference to FIG. 10, the evaluation engine 1002 manages the operation of the NLP model 1006, the machine learning engine 1016, and the event model 1008. In some examples, the structured data evaluation engine 1104 is configured to manage at least the event model 1008. In some examples, the unstructured data evaluation engine 1106 is configured to manage at least the NLP model 1006 and the machine learning engine 1016.

In particular, the structured data evaluation engine 1104 is configured to monitor, collect, receive, and evaluate data that is in a structured format. This may include data that is objective in nature and which the structured data evaluation engine 1104 recognizes upon receiving.

The unstructured data evaluation engine 1106 is configured to monitor, collect, receive, and evaluate data that is in an unstructured format. This may include data that is subjective in nature. To this end, as described herein, the unstructured data evaluation engine 1106 executes one or more techniques to identify elements (e.g., letters, symbols, numbers, verbs, adjectives, nouns, punctuation, words, order of words with respect to other words, sentence syntax, paragraph syntax, spacing between words, misspellings, grammatical mistakes, active/passive voice, and other elements of text) of spoken text and/or written text and characteristics of the spoken text and/or written text that may be relevant to their message (e.g., tone, meaning, sarcasm, feelings, inferences, impressions, attitude, outlook, positive/ negative/other, and any other characteristic). These techniques include, for example, natural language processing (NLP) using machine learning, Hidden Markov models, Dynamic time warping (DTW), neural networks, deep neural networks and other deep learning models, and any other suitable technique for identifying elements and/or characteristics of spoken text and/or written text. Other forms of unstructured data other than spoken and written text. In some examples, the unstructured data evaluation engine 1106 extracts elements, which can be considered structured data, from the unstructured data. From this, the unstructured data evaluation engine 1106 can identify relationships between the elements. These relationships can be stored and compared to similar relationships identified from unstructured data for other dependent users. Based on these relationships and/or the elements, certain predictions about the dependent user can be made.

The report generation engine 1004 is configured to evaluate the data analyzed by the evaluation engine 1002 and generate a condition report for a particular dependent user or group of dependent users. For example, the condition report may be based on one or more condition scores determined by each of the structured data evaluation engine 1104 and/or the unstructured data evaluation engine 1106. In this manner, the condition report may be based on objective data describing a dependent user's condition (e.g., vital signs, lab data, structured data extracted from unstructured data, etc.) and subjective data describing the dependent user's condition (e.g., notes from authorized users having different roles, data captured in a room in which the dependent user is staying, etc.). In some examples, the condition report indicates a likelihood that the dependent user has or will develop a particular condition. The condition report may include any suitable combination of numerical indicators, percentages, and other data that can help an authorized user treat the dependent user. The condition report, in some examples, identifies which data, structured or unstructured, affected its generation and the relative weights of each type of data. In some examples, the condition report includes an indication that the dependent user has a particular condition.

The escalation engine 1108 is configured to escalate certain condition reports. In some examples, this includes generating an instruction for the routing engine 912 to route a condition report to a particular user or group of users. In some examples, the escalation engine 1108 assigns a response time to each condition report based on the criticality and/or seriousness of the assessment. For example, if a condition report indicates that a certain dependent user has a very high likelihood of developing a cellular abnormality within a fixed period of time, the escalation engine 1108 may assign a 24 hour minimum response time to the condition report which can be provided to an authorized user by the routing engine 912 or otherwise. In some examples, providing the condition report to the authorized user includes introducing the assessment into an existing list of tasks scheduled for the authorized user (e.g., morning rounds, charting, etc.). Because the escalation engine 1108 has escalated the condition report and an associated task (e.g., check on the dependent user associated with the assessment), the authorized user may see the associated task as needing more urgent attention than other tasks.

Figure 12:
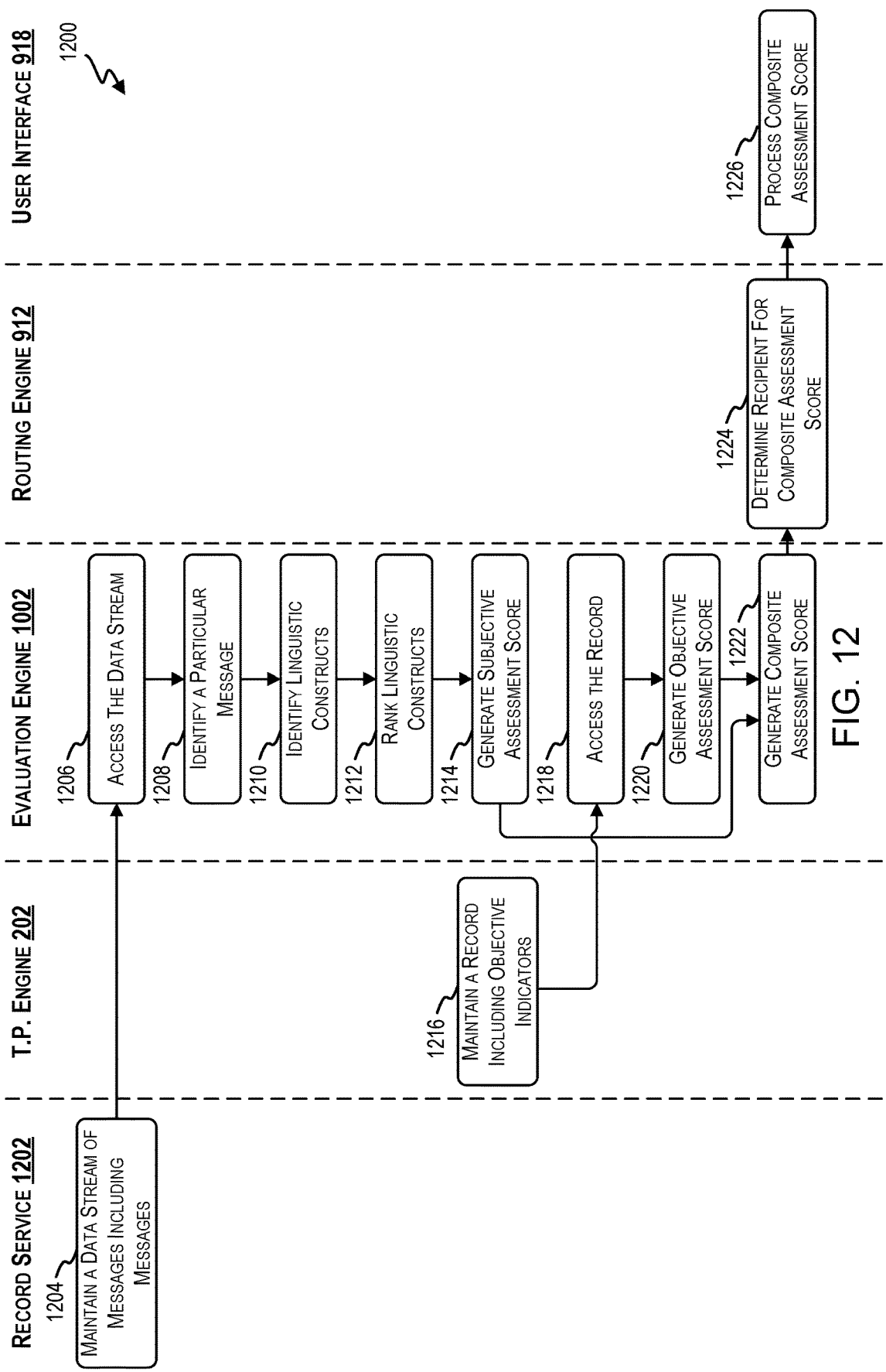
FIG. 12 is a flow diagram depicting example acts for implementing techniques relating to signal processing for making predictive determinations, according to at least one example.
Figure 13:
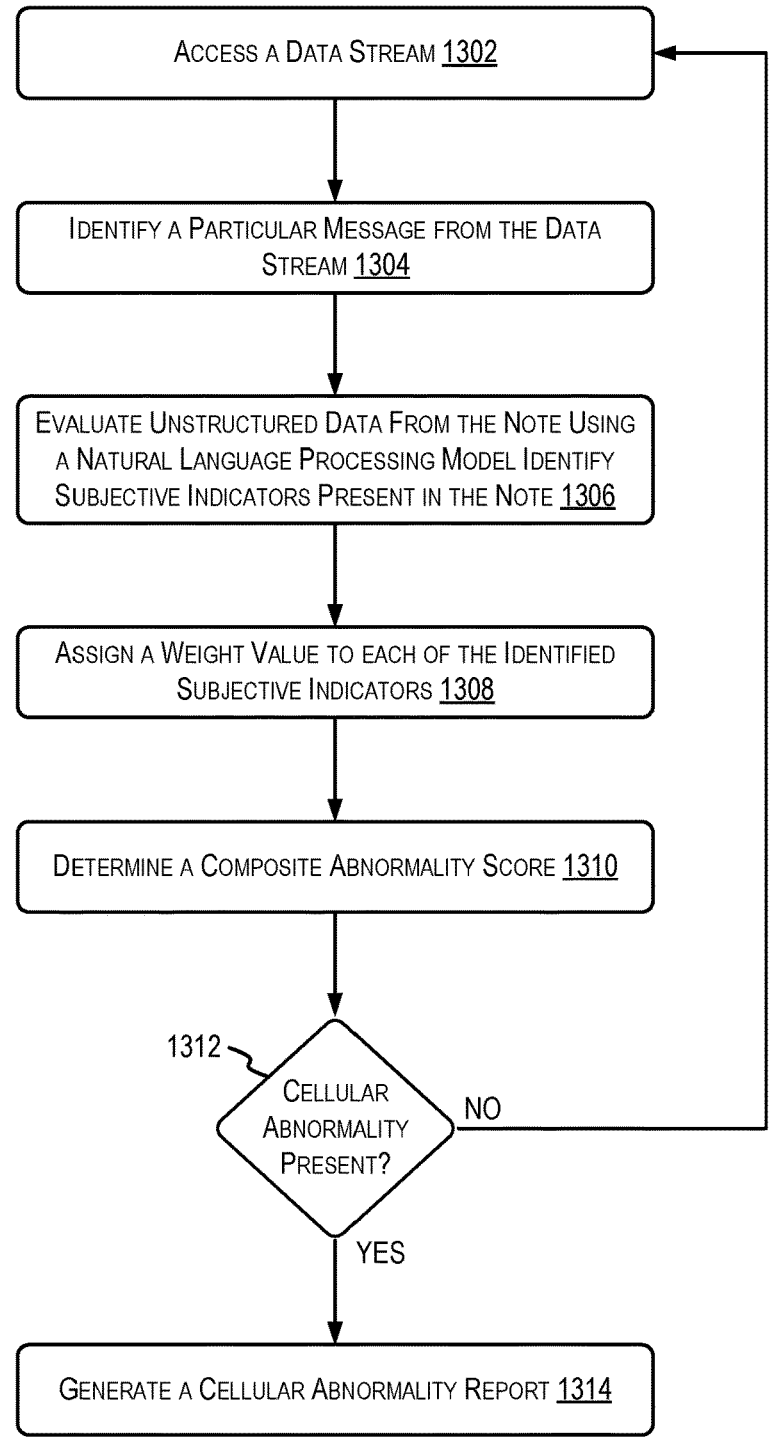
FIG. 13 is a flow diagram depicting example acts for implementing techniques relating to signal processing for making predictive determinations, according to at least one example.

FIGS. 12 and 13 illustrate example flow diagrams showing respective processes 1200 and 1300, as described herein. These processes 1200 and 1300 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

FIG. 12 depicts the process 1200 including example acts or techniques relating to determining a condition report according to an example of the disclosure. Different portions of the process 1200 may be performed by a record service 1202, the transformative processing engine 202, the evaluation engine 1002, the routing engine 912, and one or more user interfaces 918. The record service 1202 is an electronic record storage service and may be implemented by an electronic medical record (EMR). The record service 1202 is an example of one of the components 910.

The process 1200 begins at 1204 by maintaining a data stream of messages including notes. In some examples, the record service 1202 maintains the data stream. In some examples, this includes receiving messages that include the notes as they are entered by authorized users using user devices and storing the notes in association with records. In some examples, the record service 1202 maintains the data stream in about real-time. Other elements can access the data stream to implement the techniques described herein. The note can include subjective observations of a dependent user (e.g., a patient) as observed and provided by an authorized user (e.g., a clinical professional). In some examples, the note can include certain other unstructured data that describes conditions pertaining to the dependent user (e.g., recorded conversations in a dependent user's room, sensing information collected from sensors in the dependent user's room (e.g., raw sensor data, processed sensor data, and other similar data), output from devices that are being used to treat the dependent user (e.g., raw sensor data, waveform data, structure data lab data, and other similar data), and any other suitable information describing conditions pertaining to the dependent user. The note may be included as part of a record, but may accessed prior to the note being stored in association with the record. In this manner, the note may be accessed in about real-time (e.g., within seconds). In some examples, the messages comply with some industry standard such as HL7.

At 1206, the process 1200 accesses the data stream. In some examples, the predictive condition engine 902 accesses the data stream. Accessing the data stream includes, in some examples, subscribing to a service that allows the predictive condition engine 902 to analyze messages in the data stream that meet certain criteria. For example, when a new dependent user is entered in the system, certain identifying information such as a unique user identifier, a unique government identifier, a name, and any other suitable information may be provided to the service. In some examples, the accesses the data stream includes the predictive condition engine 902 pulling relevant data from the data stream. In this example, the predictive condition engine 902 may monitor the data stream and pull data (e.g., messages) that meet certain criteria (e.g., identify a dependent user and/or are related to conditions of the dependent user).

At 1208, the process 1200 identifies a particular message. In some examples, the predictive condition engine 902 identifies the particular message. The particular message may be identified from the data stream. As described herein, the data stream may include many messages that identify different dependent users and even other messages that do not identify dependent users. In some examples, the data stream may be considered a pipeline of all or almost all messages relating to a facility (e.g., a clinical facility). In this manner, some messages may relate to an electronic record of the dependent user, operation and output of equipment in the facility (e.g., heating air conditioning and ventilation equipment), operation and output of specialized equipment (e.g., diagnostic machines for identifying conditions of the dependent user), sensor data from sensors of various types (e.g., door sensors, hand wash station sensors, bed sensors, bathroom sensors, and other sensors), and any other messages. In some examples, the data stream includes messages from multiple facilities. For example, a particular organization may include many facilities and data messages may be transferred through a central hub such as the transformative processing engine 202 for processing.

As part of identifying the particular message at 1208, the process 1200 sorts through the data stream to identify those messages that are most relevant to a particular task. For example, the task may include determining whether the dependent user has or is at risk of getting a particular condition. In this example, at 1208, messages identifying the dependent user and other factors relating to the particular condition (e.g., if the condition is transmittable, information about the population of users in the facility may be relevant), which may be considered signal inputs, are identified and accessed for evaluation by the predictive condition engine 902.

In some examples, the particular message is identified at 1208 in about real-time. About real-time may indicate that the predictive condition engine 902 has access to the particular message shortly after (e.g., within a few seconds to a few minutes) the message is created (e.g., by an authorized user entering a note into the electronic record of the dependent user).

At 1210, the process 1200 identifies linguist constructs. In some examples, the predictive condition engine 902 utilizing the NLP model 1006 identifies the linguistic constructs. This includes, for example, parsing the message, which includes data about the dependent user perhaps arranged in a note, to identify linguistic constructs within the message. These linguistic constructs indicate, for example, words, definitions, parts of speech, relationships to other words, relationships between sentences, and any other suitable linguistic constructs. In some examples, the linguistic constructs may include subjective indicators and/or objective indicators. In some examples, identifying the linguistic constructs may include initializing the NLP model 1006. In some examples, the NLP model 1006 may be configured to evaluate the identified message, including the note, to determine whether the message includes facts that support a particular condition. Initializing the NLP model 1006 may include causing the NLP model 1006 to begin to evaluate the message. In some examples, the NLP model 1006 has been trained using data that corresponds to the particular condition for which the process 1200 is being performed. For example, in the case of cellular anomalies, the NLP model 1006 would have been trained using data (e.g., notes) that correspond to dependent users who developed a cellular anomaly.

At 1212, the process 1200 ranks linguistic constructs. In some examples, the predictive condition engine 902 accesses output from the NLP model 1006 to rank the linguistic constructs. This includes, for example, ranking the linguistic constructs identified at 1210. The ranking can be based on any suitable factor. For example, the ranking can be based on a relevancy to a particular condition and/or symptom of a condition. Thus, the ranking can be used to interpret the linguistic constructs in a manner that indicates assessments, plans, or sentiments of the author with respect to the condition. These assessments, plans, and sentiments include subject observations that may be explicit in the note, implied within the note, or otherwise hidden within the note.

At 1214, the process 1200 generates a subjective assessment score. In some examples, the predictive condition engine 902 generates the subjective assessment score. The subjective assessment score can be based on the linguistic constructs identified from the note. In this manner, the subjective assessment score is based on the assessments, plans, or sentiments of the authorized user that prepared the note. In some examples, the subjective assessment score indicates a likelihood that the dependent user has or will develop the condition. In some examples, the subjective assessment score corresponds to a fixed period of time in which the dependent user will likely develop the condition.

At 1216, the process 1200 maintains a record including objective indicators. In some examples, the transformative processing engine 202 maintains the record. For example, the transformative processing engine 202 can process the record and store it in a data warehouse where it can be accessed by the predictive condition engine 902. The objective indicators are examples of vital sign readings, test results, and other objective data that can be included in a dependent user's electronic record.

At 1218, the process 1200 accesses the record. In some examples, the predictive condition engine 902 accesses the record. Accessing the record can include receiving it from the transformative processing engine 202. Accessing the record can also include requesting the record from the transformative processing engine 202. In some examples, only certain objective indicators of the record are accessed. The objective indicators may correspond to a certain time period. For example, all vital signs for the last five years in the record can be accessed. In some examples, the accessed objective indicators may correspond to certain tests.

At 1220, the process 1200 generates an objective assessment score. In some examples, the predictive condition engine 902 generates the objective assessment score. Generating the objective assessment score can include initializing the event model 1008 to evaluate the objective indicators. In some examples, the event model 1008 is configured to evaluate the objective indicators to determine whether the objective indicators indicate that a dependent user has or is likely to develop a certain condition. Thus, the objective assessment score can indicate a likelihood that the dependent user has or is likely to develop a certain condition based on objective data. In some examples, the objective assessment score corresponds to a fixed period of time in which the dependent user will likely develop the condition. In some examples, the subjective assessment score and the objective assessment score correspond to the same time period.

At 1222, the process 1200 generates a composite assessment score. In some examples, the predictive condition engine 902 generates the composite assessment score. The composite assessment score can be based on the subjective assessment score and/or the objective assessment score. In some examples, generating the composite assessment score includes generating a condition report (e.g., a cellular anomaly report) that includes the composite assessment score. The composite assessment score can indicate an overall likelihood that the dependent user already has the condition or will develop the condition. In some examples, the composite assessment score corresponds to a fixed period of time in which the dependent user will likely develop the condition.

At 1224, the process 1200 determines a recipient for the composite assessment score, included in, for example, a condition report. In some examples, the routing engine 912 determines the recipient. Determining the recipient may include utilizing one or more rules within the routing engine 912 to identify the recipient based on the composite assessment score and/or the condition report. In some examples, the routing engine 912 determines a group of recipients. This can include an escalation team responsible for responding to dependent users who are at risk for the condition. In some examples, the routing engine 912 also provides the composite assessment score and/or condition report to the recipient and/or group of recipients.

At 1226, the process 1400 processes the composite assessment score. In some examples, the one or more user interfaces 918 are used to process the composite assessment score. This includes, for example, introducing the composite assessment score into an existing flow for an authorized user that accesses the one or more user interfaces 918. The existing flow can be a process by which the authorized user treats her dependent users.

FIG. 13 depicts the process 1300 including example acts or techniques relating to determining a condition report according to at least one example. The process 1300 may be performed by the predictive condition engine 902.

The process 1300 begins at 1302 by accessing a data stream. The data stream includes messages originating from a plurality of sending systems in a computer network and identify a plurality of dependent users.

At 1304, the process 1300 identifies a particular message from the data stream. The particular message may be one of the messages in the data stream. Identifying the particular message may be based on a message type associated with the particular message. In some examples, the particular message includes a note that includes an observation corresponding to a dependent user as observed and recorded by an authorized user. At least a portion of the observation can be represented as unstructured data in the note. In some examples, the note is a report that describes causes and effects associated with cellular abnormalities.

Identifying by message type may allow the system to ignore certain messages that do not include relevant information about the dependent user. Thus, the system may maintain a list of message types that either include notes and/or include other information relevant to making the determination about the cellular abnormality.

At 1306, the process 1300 evaluates the unstructured data in the note using a natural language processing model to identify subjective indicators present in the note. The subjective indicators may indicate an assessment, a plan, or sentiment of the authorized user with respect to the dependent user and a cellular abnormality. In some examples, the cellular abnormality is a cellular condition potentially present in the dependent user. The subjective indicators can include words, terms, and/or phrases that are indicative of one or more concepts associated with cellular abnormalities.

At 1308, the process 1300 assigns a weight value to each of the identified subjective indicators. In some examples, assigning the weight value is based on a respective correspondence of the identified subjective indicators to the cellular abnormality. For example, those subjective indicators that have a closer correspondence to the cellular abnormality may include a higher weight value.

At 1310, the process 1300 determines a composite abnormality score. In some examples, determining the composite abnormality score is based on the weight values of the identified subjective indicators and relationships between the identified subjective indicators. The composite abnormality score can correspond to a presence of the cellular abnormality in the dependent user.

At 1312, the process 1300 determines whether a cellular abnormality is present in the dependent user. In some examples, this may be based on a first comparison of the composite abnormality score with a normality threshold. The normality threshold may be a specific to certain classes of dependent users or may be normalized for all dependent users. If the answer at 1312 is NO, the process 1300 returns to 1302 to access the data stream. This may include accessing the data stream to monitor messages relating to the same dependent user or same set of dependent users or a different dependent user or a different set of dependent users. If the answer at 1312 is YES, the process 1300 continues to 1314.

At 1314, the process 1300 generates a cellular abnormality report. The cellular abnormality report can identify at least the presence of the cellular abnormality and the dependent user. In some examples, the cellular abnormality report further identifies the particular type of cellular abnormality.

In some examples, the process 1300 further includes determining, based on the weight values of the identified subjective indicators and the relationships between the identified subjective indicators, a plurality of type scores corresponding to a plurality of cellular abnormality types to which the cellular abnormality potentially belongs. In this example, the process 1300 further includes determining, based on a second comparison of the plurality of type scores with respective type thresholds, that the cellular abnormality present in the dependent user is a particular type of cellular abnormality of the plurality of cellular abnormality types. In this manner, the process 1300 determines "if" the dependent user has the cellular abnormality and, if so, determines "which" cellular abnormality from a predefined set of cellular abnormalities.

In some examples, the process 1300 further includes adding the cellular abnormality report to a validation queue. In this example, the process 1300 further includes allowing the authorized user or a different authorized user to access the cellular abnormality report from the validation queue.

In some examples, the process 1300 further includes providing the cellular abnormality report to a user device accessible by the authorized user. In this manner, the authorized user can review and validate the report. In some examples, the cellular abnormality report includes at least a portion of the note. In this example, the process 1300 further includes, prior to providing the cellular abnormality report to the user device, graphically highlighting at least a portion of the identified subjective indicators present in the portion of the note. In this manner, the authorized user or other user can easily see which subjective indicators (e.g., words, sentences, terms, values, etc.) in the note were considered by the system to make the determination at 1310 and 1312. In some examples, the assigned weight values are also presented along with the subjective indicators. The graphical presentation may include different colors, styles, and the like to distinguish certain subjective indicators from each other and from other text that was not considered in the determinations.

Specific details are given in the above description to provide a thorough understanding of the examples. However, it is understood that the examples may be practiced without these specific details. For example, circuits may be shown in block diagrams in order not to obscure the examples in unnecessary detail. In other instances, well-known circuits, processes, algorithms, structures, and techniques may be shown without unnecessary detail in order to avoid obscuring the examples.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the examples may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, examples may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed:

1. A system comprising:
   memory configured to store computer-executable instructions; and
   one or more processors configured to access the memory to execute the computer-executable instructions to perform operations comprising:
   accessing messages in a data stream, the messages originating from a plurality of computer systems in a computer network, the plurality of computer system comprising electronic devices that generate the messages to be transmitted via the computer network;
   identifying first identified data from a first message from the accessed messages, and determining that the first identified data corresponds to a first entity, where the first message is from a first system of the plurality of computer systems;
   identifying second identified data from a second message from the accessed messages, and determining that the second identified data also corresponds to the first entity, where the second message is from a second system of the plurality of computer systems;
   aggregating data from the accessed messages determined to correspond to the first entity, the aggregated data comprising the first identified data and the second identified data;
   selecting a subset of data from the aggregated data, including the first identified data and the second identified data;
   generating a report corresponding to the first entity to comprise the selected subset of data, including:
   ephemeral data from one or both of the first identified data and the second identified data that is tagged to be removed from the report at a predetermined time; and
   persistent data from one or both of the first identified data and the second identified data that is not to be removed from the report at the predetermined time;
   providing access to the report via one or more interfaces; and removing the ephemeral data from the report based at least in part on the predetermined time.

2. The system as recited in claim 1, the operations further comprising:
causing transmission of the report to one or more destination devices to facilitate the providing the access.

3. The system as recited in claim 2, where the one or more destination devices correspond to one or both of the first system and the second system, and the report is transmitted to one or both of the first system and the second system.

4. The system as recited in claim 3, the operations further comprising:
removing a portion of the report as a function of a requirement of the first system or the second system before transmitting the report to the first system or the second system.

5. The system as recited in claim 4, the operations further comprising:
generating first de-identified data based at least in part on the first identified data; and
generating statistical data at least partially by aggregating the first de-identified data for the first entity with second de-identified data for a second entity.

6. The system as recited in claim 5, where the transmission comprises the statistical data.

7. The system as recited in claim 6, where the generating the report comprises generating a longitudinal history corresponding to the first entity, the report comprising the longitudinal history.

8. A computer-implemented method comprising:
accessing, by a computer system communicably couplable via a computer network with a plurality of computer systems comprising electronic devices that generate messages to be transmitted via the computer network toward a plurality of different destination devices, messages in a data stream, the messages originating from the plurality of computer systems in the computer network;
identifying, by the computer system, first identified data from a first message from the accessed messages, and determining that the first identified data corresponds to a first entity, where the first message is from a first system of the plurality of computer systems;
identifying, by the computer system, second identified data from a second message from the accessed messages, and determining that the second identified data also corresponds to the first entity, where the second message is from a second system of the plurality of computer systems;
aggregating, by the computer system, data from the accessed messages determined to correspond to the first entity, the aggregated data comprising the first identified data and the second identified data;
selecting, by the computer system, a subset of data from the aggregated data, including the first identified data and the second identified data;
generating, by the computer system, a report corresponding to the first entity to comprise the selected subset of data, including:
ephemeral data from one or both of the first identified data and the second identified data that is tagged to be removed from the report at a predetermined time; and
persistent data from one or both of the first identified data and the second identified data that is not to be removed from the report at the predetermined time;

providing, by the computer system, access to the report via one or more interfaces; and
removing, by the computer system, the ephemeral data from the report based at least in part on the predetermined time.

9. The computer-implemented method as recited in claim 8, further comprising:
causing, by the computer system, transmission of the report to one or more destination devices to facilitate the providing the access.

10. The computer-implemented method as recited in claim 9, where the one or more destination devices correspond to one or both of the first system and the second system, and the report is transmitted to one or both of the first system and the second system.

11. The computer-implemented method as recited in claim 10, further comprising:
removing, by the computer system, a portion of the report as a function of a requirement of the first system or the second system before transmitting the report to the first system or the second system.

12. The computer-implemented method as recited in claim 11, further comprising:
generating, by the computer system, first de-identified data based at least in part on the first identified data; and
generating, by the computer system, statistical data at least partially by aggregating the first de-identified data for the first entity with second de-identified data for a second entity.

13. The computer-implemented method as recited in claim 12, where the transmission comprises the statistical data.

14. The computer-implemented method as recited in claim 13, where the generating comprises generating a longitudinal history corresponding to the first entity based at least in part on the aggregated data, the report comprising the longitudinal history.

15. One or more non-transitory, machine-readable storage media comprising machine-executable instructions that, when executed by one or more processing devices, cause the one or more processing devices to perform operations comprising:
accessing messages in a data stream, the messages originating from a plurality of computer systems in a computer network;
identifying first identified data from a first message from the accessed messages, and determining that the first identified data corresponds to a first entity, where the first message is from a first system of the plurality of computer systems;
identifying second identified data from a second message from the accessed messages, and determining that the second identified data also corresponds to the first entity, where the second message is from a second system of the plurality of computer systems;
aggregating data from the accessed messages determined to correspond to the first entity, the aggregated data comprising the first identified data and the second identified data;
selecting a subset of data from the aggregated data, including the first identified data and the second identified data;
generating a report corresponding to the first entity to comprise the selected subset of data, including:

ephemeral data from one or both of the first identified data and the second identified data that is tagged to be removed from the report at a predetermined time; and persistent data from one or both of the first identified data and the second identified data that is not to be removed from the report at the predetermined time;

providing access to the report via one or more interfaces; and removing the ephemeral data from the report based at least in part on the predetermined time.

16. The one or more non-transitory, machine-readable storage media as recited in claim 15, the operations further comprising:

causing transmission of the report to one or more destination devices to facilitate the providing the access.

17. The one or more non-transitory, machine-readable storage media as recited in claim 16, where the one or more destination devices correspond to one or both of the first system and the second system, and the report is transmitted to one or both of the first system and the second system.

18. The one or more non-transitory, machine-readable storage media as recited in claim 17, the operations further comprising:

removing a portion of the report as a function of a requirement of the first system or the second system before transmitting the report to the first system or the second system.

19. The one or more non-transitory, machine-readable storage media as recited in claim 18, the operations further comprising:

generating first de-identified data based at least in part on the first identified data; and generating statistical data at least partially by aggregating the first de-identified data for the first entity with second de-identified data for a second entity.

20. The one or more non-transitory, machine-readable storage media as recited in claim 19, where the transmission comprises the statistical data.

\* \* \* \* \*